Figure 1:
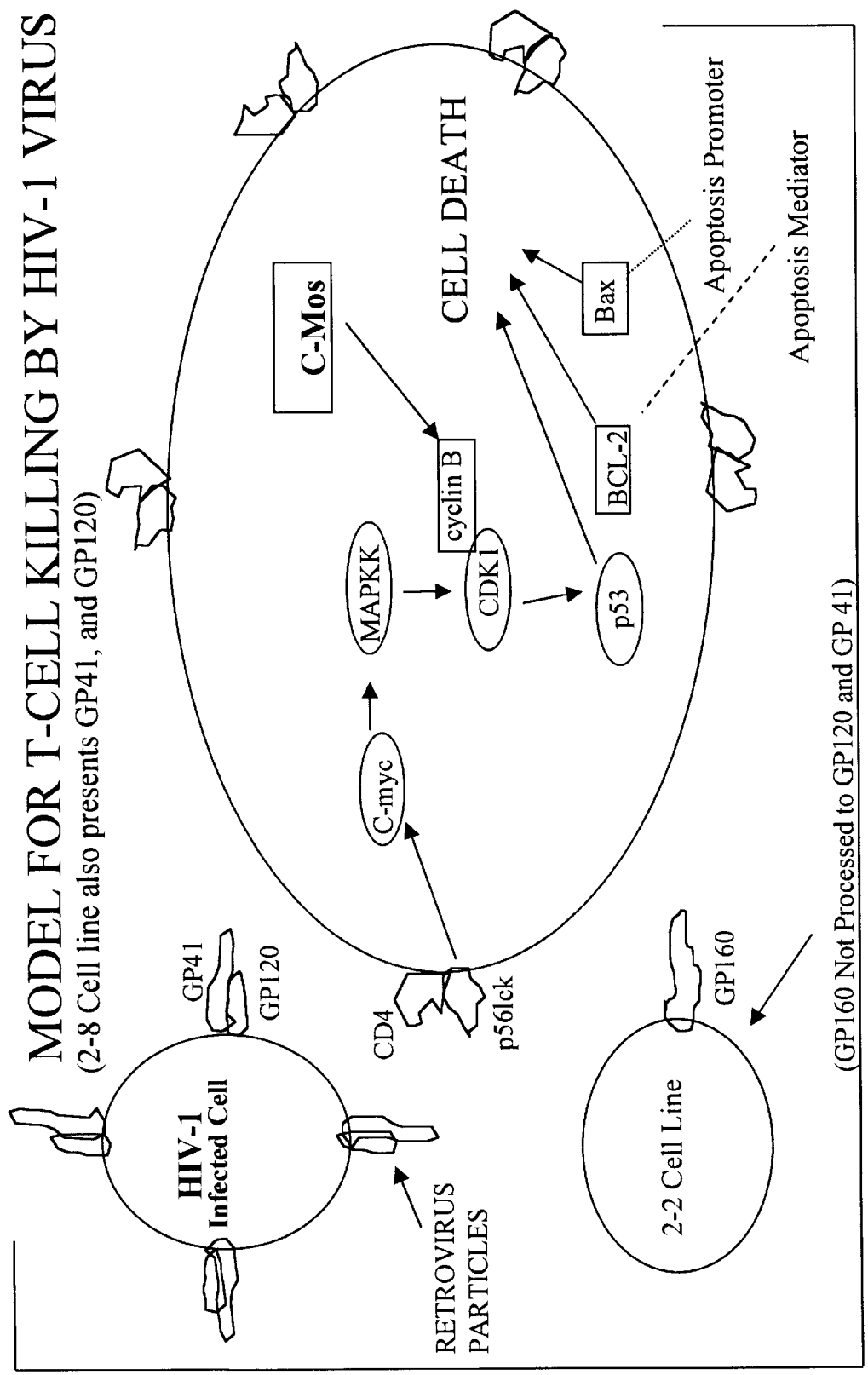

United States Patent [19]

Wheelock et al.

[11] Patent Number: 5,833,994
[45] Date of Patent: Nov. 10, 1998

[54] USE OF THE AH RECEPTOR AND AH RECEPTOR LIGANDS TO TREAT OR PREVENT CYTOPATHICITY OF VIRAL INFECTION

[75] Inventors: Geoffrey D. Wheelock; Joseph Rininger; John G. Babish; Padmasree Chigurupati, all of Ithaca, N.Y.

[73] Assignee: Paracelsian, Inc., Ithaca, N.Y.

[21] Appl. No.: 780,742

[22] Filed: Jan. 8, 1997

[51] Int. Cl.⁶ .................................................. A01N 65/00
[52] U.S. Cl. ................................. 424/198.1; 424/184.1
[58] Field of Search ........................... 424/184.1, 195.11, 424/198.1

[56] References Cited

FOREIGN PATENT DOCUMENTS

96/17605   6/1996   WIPO .

OTHER PUBLICATIONS

El–Mekkawy et al. "Inhibitory Effects of Egyptian Folk Medicines on Human Immunodeficiency Virus (HIV) Reverse Transcriptase", *Chemical and Pharmaceutical Bulletin*, vol. 43, No. 4(Apr. 1995), pp. 641–648. RS1.C4 Abstract Only.
Mucsi et al. "Combined Effects of Flavonoids and Acyclovir Against Herpesviruses in Cell Cultures", *Acta Microbiologica Hungarica*, vol. 39, No. 2(1992), pp. 137–147. Abstract Only.
Serra et al. "Antiviral Activity of New Triterpenic Derivatives", *Pharmacological Research*, vol. 29, No. 4 (1994 May–Jun.), pp. 359–366. RS122.P45. Abstract Only.
Kerksiek et al. "Interaction of Cryptophycin 1 with Tubulin and Microtubules", *FEBS Letters*, vol. 377, No. 1 (1995 Dec. 11), pp. 59–61. QP501.F4.
Ono et al. "Differential Inhibitory Effects of Various Flavonoids on the Activities of Reverse Transcriptase and Cellular DNA and RNA Polymerases [published erratum appears in Eur J Biochem 1991 Aug. 1;199(3):769]", *European Journal of Biochemistry*, vol. 190, No. 3(Jul. 5, 1990), pp. 469–476. QP501.E89. Abstract Only.
Bauman, J.W. et al, (1995) Inhibitory Effects of 2,3,7, 8–Tetrachlorodibenzo–p–dioxin on Rat Hepatocyte Proliferation Induced by 2/3 Partial Hepatectomy, Cell Proliferation 28: pp. 437–451.
Bjeldanes, L.F. et al, (1991) Aromatic hydrocarbon responsiveness–receptor agonists generated from indole–3–carbinol in vitro and in vivo: Comparisons with 2,3,4,8–tetrachlorodibenzo–p–dioxin, Proc. Natl. Acad. Sci. USA 88:9543–9547.
Cohen, D.I. et al, (1992) Participation of Tyrosine Phosphorylation in the Cytopathic Effect of Human Immunodeficiency Virus–1, Science, 256: pp. 542–545.
Connor, R.I. et al, (1993) Increased Viral Burden and Cytopathicity Correlate Temporally with CD4+ T–Lymphocyte Decline and Cinical Progression in Human Immunodeficiency Virus Type 1–Infected Individuals, Journal of Virology, 67: pp. 1772–1777.

Corbeil, J., et al, (1996) HIV–Induced Apoptosis Requires the CD4 Receptor Cytoplasmic Tail and Is Accelerated by Interaction of CD4 with p561ck, Jour. Of Experimental Medicine, 183: pp. 39–48.
DeVito, M.J., et al, (1994) Dose–Response Relationships in Mice Following Subchronic Exposure to 2,3,7, 8–Tetrachlorodibenzo–p–dioxin: CYP1A1, CYP1A2, Estrogen Receptor, and Protein Tyrosine Phosphorylation, Toxicology and Applied Pharmacology, 124: pp. 82–90.
Fernandez–Salguero, P., et al, (1995) Immune System Impairment and Hepatic Fibrosis in Mice Lacking the Dioxin–Binding Ah Receptor, Science, 268: pp. 722–726.
Gasiewicz, T.A. et al, (1995), Alpha–Naphithoflavone acts as an antoagonist of 2,3,7,8–tetrachloro–dibenzo–p–dioxin by forming an inactive complex with the Ah receptor., Molecular Pharmacology 40: 607–612.
Heinkelein, M. Et al, (1995) Contact of Human Immunodeficiency Virus Type 1–Infected and Uninfected CD4+ T Lymphocytes is Highly Cytolytic for Both Cells, Journal of Virology 69: pp. 6925–6931.
Hivroz, c. Et al, (1993) Human Immunodeficiency Virus gp120 and Derived Peptides Activate Protein Tyrosine Kinase p561ck in Human CD4 T Lymphocytes, European Journal of Immunology 23: 600–607.
Jellinck, P.H., et al, (1993) Ah receptor binding properties of indole carbinols and induction of hepatic estradiol hydroxylation, Biochem. Pharmacol., 45: 1129–1136.
Kleman, M.I. et al, (1994), Regulation of human dioxin receptor function by indolocarbazoles, receptor ligands of dietary origin, J. Of Biol. Chem., 269: 5137–5144.

(List continued on next page.)

Primary Examiner—Jeffrey Stucker
Attorney, Agent, or Firm—Brown, Pinnisi & Michaels, PC

[57] ABSTRACT

The present invention includes the method of treating a viral infection, specifically one occurring as a result of infection by a human immunodeficiency virus (HIV-1). The method of treatment depends upon the ligand binding of the Ah receptor. Transformation and translocation of the receptor and DNA binding are not required. The study of compounds that interact with the Ah receptor, either as agonists, or antagonists, has resulted in the identification of compounds with useful therapeutic properties through perturbation of viral pathogenic signal transduction pathways. Antagonists of the Ah receptor are more likely candidates for treatment because the toxicity of such compounds is low. Identification of molecules affecting cellular targets, such as the Ah receptor, that inhibit viral pathologic signaling would be of great therapeutic potential as the activity of these molecules is not directed against the virus itself, therefore genetic viral mutation to escape such therapy would be far less likely to occur. The use of secondary compounds for use in combinational, synergistic, therapy is also enclosed. These second compounds are also known to have some effect on the treatment of cellular pathologic changes, together with those compounds found to be effective upon the regulation of the Ah receptor the compounds can more beneficially control virally induced cellular cytopathic changes.

31 Claims, 2 Drawing Sheets

OTHER PUBLICATIONS

Kowalski, M. Et al, (1991), Attenuation of Human Immunodeficiency Virus Type 1 Cytopathic Effect by a Mutation Affecting the Transmembrane Envelope Glycoprotein, Journal of Virology 65: 281–291.

Landers, J.P et al, (1991), The Ah receptor and the mechanism of dioxin toxicity, Biochem J. 276: 273–278.

Lu, Y.F. et al, (1995) Identification of 3'–methoxy–4'–nitroflavone as a pure aryl hydrocarbon (Ah) receptor antagonist and evidence for more than one form on the nuclear Ah receptor in MCF–7 human breast cancer cells, Arch. Biochem Biophys., 316: 470–477.

Ma, X. Et al, (1992), Protein Tyrosine Phosphrylatio as a Indicator of 2,3, 7, 8–Tetrachloro–p–Dioxin exposure In Vivo and In Vitro, Biochemical and Biophysical Research Comm. 189):(1) pp. 59–65.

Ma, X. Et al, (1993), Acuate 2,3,7,8–Tetrachlorodibenzo–p–Dioxin Exposure Results in Enhanced Tyrosylphosphorylation and Expression of Murine Hepatic Cyclin Dependent Kinases, Biochem and Biophysical Research Communications.

Merchant, M. Et al, (1995) In vitro inhibition of 2,3,7, 8–tetrachlorodibenzo–p–dioxin–induced activity by alpha–naphthoflavone and 6–methyl– 1,3,8– trichlorodibenzofuran using an aryl hydrocarbon (Ah)–responsive construct, Biochem. Pharmacol. 50:663–668.

Poland, A. Et al, (1976), Sterospecific, high affinity binding of 2,3, 7, 8–tetrachlorodibenzo–p–dioxin by hepatic cytosol. Evidence that the binding species is receptor for induction of aryl hydrocarbon hydroxylase, J. Biol Chem. 251: 4936–4946.

Tani, Y. Et al, (1993), Normal T. Cell Receptor–Mediated Signaling in T Cell Lines Stably Expressing HIV–1 Envelope Glycoproteins, Journal of Immunology, 151: 7337–7348.

Wheelock, G.D. et al, (1996) Bioimmunoassay of Aryl Hydrocarbon (Ah) receptor Transformation in vitro by 2,3,7, 8–tetrachlorodibenzo–p–dioxin (TCDD), Toxicol. Methods 6:41–50.

Zacharewski, T. Et al, (1989), Induction of cytochrome P450–dependent monooxygenase activities in rat hepatoma H–4–HE cells in culture by 2,3,7,8–tetrachlorodibenzo–p–dioxin and related compounds; mechanistic studies using radiolabeled congeners, Arch. Biochem. Biophys. 272:344–355.

Bouton, A. H. Et al, 1991, Tryosine Phosphorylation of Three Cellular Proteins Correlates With Transformation of Rat 1 Cells by $pp60^{src}$, Molecular Carcinogenesis 4: 145–152.

Farber, E., 1986, Chemical Carcinogenesis: The Liver as a Model[1], Patho. Immumopathol. Res., 5:1–28.

Scambia, G., et al, (1993) Quercetin Induces Type–II Estrogen–Binding Sites in Estrogen–Receptor–Negative (MDA–MB231) and Estrogen–Receptor–Positive (MCF–7) Human Breast–Cancer Cell Lines.Int. J. Cancer: 54,462–466.

Dunnick, June K. & Hailey, James R. (1992) Toxicity and Carcinogenicity Studies of Quercetin, a Natural Component of Foods, Fundamental and Applied Toxicology 10, 423–431.

Astroff, B., et M., 6–Methyl–1, 3, 8–trichlorodibenzofuran as a 2, 3, 7, 8–Tetrachlorodibenzo–p–dioxin Antagonist: Inhibition of the Induction of Rat qtochrome P–450 Isozymes and Related Monooxygenase Activities, Mol. Pharm., 33:231–36 (1988).

Bannister, R., et al., 6–Methyl–1, 3, 8–'trichlorodibenzofuran as a 2, 3, 7 8Tetrachlorodibenzo–p–dioxin Antagonist in C57BL16 Mice, Toxicology 54:139–50 (1989).

Bartlett, R. and P. Nurse, Yeast as a model system for understanding the control of DNA replication in Eukaryotes, Bioessays 12: 457–463 (1990).

Choudhury, B.R., S.J. Haque, and M.K. Poddar (1987 In vivo and in vitro effects of kalmegh (Andrographis paniculata) extract and andrographolide on hepatic microsomal drug metabolizing enzymes,) Planta Med. 53: 135–140.

Cohen, D.I., E. Donoghue, H. Tian, V. Kolesnitchenko, H.C. Lane, and L. Wahl (1993) A biochemical program implicated in HIV–1 envelope–mediated cell death, Int. Conf. AIDS 9: 200.

Draetta, G., H. Piwnica–Worms, D. Morrison, B. Druker, T. Roberts, and Beach D., Human cdc2 protein kinase is a major cell–cycle regulated tyrosine kinase substrate,Nature 336: 738–744 (1988).

Draetta, G., Cell cycle control in eukaryotes: molecular mechanisms of cdc2, Trends. Biochem. Sci. 15: 378–383 (1990).

Embretson, J., et al., Massive cove?y infection helper T lymphocytes and Macrophages by by HIV during the Incubation Period of AIDS, Nature 362:359–62 (1993).

Furukawa, Y., H. Piwnica–Worms, T.J. Ernst, Y. Kanakura, and J.D. Griffin, cdc2 gene expression at the G] to S transition in hwna,. T lymphocytes, Science 250: 805808 (1990).

Handa, S.S. and A. Sharma, Hepatoprotecive activity of andrographolide against galactosamine & paracetamol intoxication in rats, Indian J. Med. Res 92: 284–292.

Harper, M.E. et al., Detection of lymphocytes expressing human T–lymphotropic virus type III in lymph nodes and peripheral bloodfrom infected individuals by in situ hybridization, Proc. Natl. Acad. Sci. 83:772 (1986).

Keyomarsi, K. and A.B. Pardee, Redundant cyclin overexpression and gene amplification in breast cancer cells, Proc. Natl. Acad. Sci. U. S. A. 90: 1112–1116 (1993).

Leibovitch, S.A., Guillier, M., Lenormand, J.L., and Leibovitch, M.P., p34cdc2 protein is complexed ivith the c–mos protein in rat skeletal muscle, Oncogene. 8, 2361–2369 (1993).

Loyer, P., D. Glaise, S. Cariou, G. Baffet, L. Meijer, and C. Guguen–Guillouzo, apression and activation of cdks (I and 2) and cyclins in the cell cycle progression during the liver regeneration, J. Biol. Chem. 269: 2491–2500 (1994).

Matsuda, T., M. Kuroyanagi, S. Sugiyama, K. Umehara, A. Ueno, and K. Nishi, Cell differentiation–inducing diterpenesfrom An4drographis paniculata Nees, Chem. Pharm. Bull (Tokyo). 42: 1216–1225 (1994).

Norbury, C. and P. Nurse, Controls of cell proliferation in yeast and animals, Ciba. Found. Symp. 150: 168–77 (1990).

Norbury, C., J. Blow, and P. Nurse, Regulatory phosphorylation of the p34cdc2 protein kinase in vertebrates, EMBO J. 10: 3321–329(1991).

Norbury, C. and P. Nurse, Animal cell cycles and their control, Annu. Rev. Biochem 61: 441–470 (1992).

Pardee, A.B., GI events and regulation of cell proliferation, Science 246: 603–608 (1989).

Pham, C.D., Arlinghaus, R.B., Zhen, C–F, Guan, K–L and Singh, B., *Characterization of MEKI phosphorylation by the V–Mos protein,* Oncogene 10:1683–1688 (1995).

Schnittman, S.M., et al., *The Resevoir for HIV–1 in Human Per Pheral Bloos Is a T cell that Maintains Expression of CD4,* Science 245:305–08 (1989).

van den Heuvel, S. and E. Harlow, *Distinct roles for cyclin–dependent kinases in cell cycle control,* Science 262: 2050–2054 (1993).

Watson, M.H., S.L. Venance, S.C. Pang, and A.S. Mak, *Smooth muscle cell proliferation. Expression and kinase activities of p34cdc2 and mitogen–activated protein kinase homologues,* Circ. Res 73: 109–117 (1993).

Williams, R.T., D.A. Carbonaro–Hall, and F.L. Hall, *Co–purification of p34cdc21p58cyclin A proline–directed protein kinase and the retinoblastoma tumor susceptibility gene product: interaction of an oncogenic serinelthreonine protein kinase with a turnor–suppressor protein,* Oncogene. 7: 423–432 (1992).

Zacharewski, T. et al., *6–Methyl–1, 3, 8–trichlorodibenzofi-tran (MCDF) as an A ntiestrogen in Human and Rodent Cancer Cell Lines: Evidence for the Role of the Ah Receptor,* Tox. Appl. Pharm., 113:311–318 (1992).

Babish and Ma, Use of Andrographolide Compounds To Treat or Prevent Pathogenicity of Disease, s/n PCT/US95/15915.

Astroff, B., & Safe, *6–Substituted–1, 3, 8–trichlorodibenzofuran as a 2, 3, 7, 8–Tetrachlorodibenzo–p–dioxin Antagonist in the Rat: Structure Activity Relationships, Toxicology,* 59:285–96 (1989).

Ross et al. "Contaminant–related Suppression of Delayed–type Hypersensitivity and Antibody Responses in Harbor Seals Fed Herring from the Baltic Sea", *Environmental Health Perspectives,* vol. 103, No. 2(1995 Feb.), pp. 162–167. Abstract Only.

Tsyrlov et al. "Stimulatory Effect of the CYP1A1 Inducer 2,3,7,8–Tetrachlorodibenzo–p–Dioxin on the Reproduction of HIV–1 in Human Lymphoid Cell Culture", *Xenobiotica,* vol. 23, No. 4(1993 Apr.), pp. 457–467. Abstract Only.

Loadman et al. "Pharmacokinetic Drug Interactions with Anticancer Drugs", Clinical Pharmacokinetics, vol. 26, No. 6 (1994 Jun.), pp. 486–500. Abstract Only.

Cohen et al. "Cocktail Attenuation of Rotational Ablation Flow Effects (CARAFE) Study: Pilot", Catheterization and Cardiovascular Diagnosis, (1996) Suppl 3, pp. 69–72. Abstract Only.

5,833,994

USE OF THE AH RECEPTOR AND AH RECEPTOR LIGANDS TO TREAT OR PREVENT CYTOPATHICITY OF VIRAL INFECTION

FIELD OF THE INVENTION

This invention pertains to the use of the aryl hydrocarbon (Ah) receptor protein complex as a drug target, alone or in combination with another compound, to treat cytopathic cell changes and viral infections generally, and the T cell depletion (cytopathicity) that occurs from infection with the human immunodeficiency virus-1 (HIV), specifically.

BACKGROUND OF THE INVENTION

1. Cell Cycle Regulation

Since the present invention relates to the discovery of compounds capable of binding, and thereby inhibiting, the aryl hydrocarbon receptor, it is important to understand its role in effectuating many cytopathic events. To do this, key aspects of cell cycle regulation should be presented.

Over the past few years cell biologists have made remarkable progress in identifying the molecules that drive the cell cycle: the carefully choreographed series of events that culminates in cell division. In doing so they have not only provided a better understanding of one of the most fundamental of the cell's activities, they have also opened a new direction for research aimed at pinpointing the cytopathicity of cancer, AIDS, angiogenesis, and a variety of viral diseases associated with cancer or oncogenesis. The reason for this intriguing convergence is that accumulating data indicates that derangement's in the cell cycle machinery may contribute to the pathology of a number of apparently unrelated diseases.

A family of cell division control enzymes termed cyclin-dependent kinase's (CDKs), along with the cyclin proteins, serves to control and coordinate the molecular events of cell division in all eukaryotic cells (Norbury and Nurse, 1992; Draetta, 1990; Draetta et al., 1988; Bartlett and Nurse, 1990). Although twelve CDKs have been described, CDK1 kinase remains the most actively studied because of its central role in the control of cell division in both yeast and animal cells (Draetta, 1990; van den Heuvel and Harlow, 1993; Pines and Hunter, 1990; Norbury and Nurse, 1990).

In normal resting cells CDK1 is not expressed or expressed at very low levels, but concentrations of CDK1 increase as the cell enters and passes through G1 and the G1/S transition. CDK1 concentrations reach maximal levels in the S, G2 and M phases (Loyer et al., 1994). As used herein, the word "expression" refers to the level of active protein of any particular protein; expression of a protein may be affected by a variety of factors including changes in transcription, translation and protein catalysis.

In association with cyclin B, CDK1 is the serine/threonine kinase subunit of M-phase-promoting factor (MPF); active MPF triggers the G2/M transition in species ranging from yeast to humans (Brizuela et al., 1989; Draetta, 1990). Several studies also suggest that CDK1 functions in the control of the G1/S transition and as well as the initiation of mitosis (Furukawa et al., 1990; Krek and Nigg, 1991).

The role of CDK proteins is completely dependent upon their expression and kinase activity in the cell cycle. CDK1 kinase activity during the cell cycle is regulated primarily through post-translational modifications including cycles of phosphorylation and dephosphorylation (Ducommun et al., 1991; Norbury et al., 1991) and interactions with cyclins (Booher and Beach, 1987; Ducommun et al., 1991; Williams et al., 1992). Intracellular compartment translocation has also been demonstrated to regulate the substrate availability of the CDK1 protein (Williams et al., 1992; Pines and Hunter, 1991).

The functioning of CDK1 involves the coordination of all events relating to cell division. In this role CDK1 is the central information processing protein. As the cell moves through the cell cycle, information concerning the activities of the cell are sent to CDK1 and as long as these signals indicate proper functioning of the cell, movement through the cell cycle continues. However, should information sent to CDK1 indicate a problem with the cell (e.g. DNA damage, microtubule disruption) progression through the cell cycle would be halted. The block is imposed on the cell cycle at either the G1/S or G2/M interphase.

An increase in CDK1 expression is seen when the cell transforms into a tumor cell. The cellular expression of CDK1 is governed by exposure to cytokines and hormones; the expression of CDK1 is one signal to the cell to initiate the events of cell division. If the events of cell division are operating normally, CDK1 levels will decrease (through specific proteolytic enzymes) and the cell will re-enter the resting state.

However, if the events of cell division are not functioning normally and CDK1 concentrations in the cell remain elevated, cellular processes will be activated that block in cell at the G1/S interphase of the cell cycle. This block is mediated through the p53 protein and involves the formation of a complex with p21 and CDK1 that inhibits the kinase activity of CDK1. The inhibition of the kinase activity of CDK1 essentially blocks the flow of information from this coordinator of cell division and the cell remains in a G1/S stasis until concentrations of CDK1 can be reduced and the cell enters a resting state.

A number of pathologies have been identified with the over expression of CDK1 protein. Increasing evidence supports the relationship of aberrant CDK1 expression and cancer (Yasui et al., 1993; Pardee, 1989). Over expression of CDK1 was noted in 90% of breast tumor cell lines examined (Keyomarsi and Pardee, 1993), in all 40 human cancer lines studied (Bartek et al., 1993) and in all clinical gastric and colon carcinomas examined (Yasui et al., 1993). Proliferation of vascular endothelial cells is mediated through CDK1 expression (Zhou et al., 1994); such stimulation is associated with angiogenesis and functions in the pathology associated with occlusion of arteries following trauma such as angioplasty (Morishita et al., 1994).

CDK1 is also implicated in HIV-1 envelope-mediated cell death. It has been demonstrated that during HIV-1 mediated cytopathogenicity, CD4+T cells were killed by a mechanism involving functional CDK1. Inhibition of the tyrosine phosphorylation of CDK1 (a step performed in early G1) resulted in an inhibition of the killing of CD4+T-cells (Cohen et al., 1993). Such a mechanism may also be involved in the cytopathogenicity of other viral diseases such as hepatitis or herpes.

2. HIV-1

Human immunodeficiency virus-1 (HIV) infection results in the development of acquired immunodeficiency syndrome (AIDS). AIDS is characterized by a compromised immune system attributed to the systemic depletion of CD4 +T lymphocytes (T cells) and S unresponsiveness of remaining CD4+T cells. The level of CD4+T cells serves as a diagnostic indicator of disease progression. HIV infected CD4 +T cells are known to be directly cytopathic to other CD4+T lymphocytes and this single cell killing event is initiated via HIV envelope protein (gp120/41) interaction with the CD4 molecule. Highly virulent isolates of HIV induce syncytia (defined as >4 nuclei within a common cell membrane), a process associated with rapid loss of CD4+T cells and disease progression. Syncytia formation requires the proteolytic processing of the gp160 envelope precursor, stable association and cell surface expression of the gp120 and gp41 subunits, CD4 binding, and membrane fusion events that follow CD4 binding. These interactions represent a key mechanism of T cell depletion during progressive HIV infection that can occur when only 1 in 1,000 to 1 in 10,000 lymphocytes are productively infected with virus (Harper, M. E. et al., 1986). This accentuates the importance of gp120/41-mediated single cell killing that can occur during HIV infection.

T lymphocyte cell lines that express unprocessed HIV envelope glycoprotein (HIVenv 2-2) or processed HIV envelope glycoprotein (HIVenv 2-8) have been developed and characterized (Tani, 1993, incorporated herein by reference). The HIVenv 2-2 cell line is unable to process the HIV envelope gene (gp160) into gp120 and gp41 and thus is incapable of killing CD4+T lymphocytes. The cell line HIVenv 2-8, however, does process the envelope gene into gp120 and gp41 subunits into HIV-like infected T cells. The proper processing of the HIV envelope protein has been shown to induce the killing of CD4+Jurkat T cells in vitro (Tani, 1993). This methodology mimics CD4+T lymphocyte depletion that, occurs in progressive HIV infection resulting in immune dysfunction.

Co-incubation of CD4+T lymphocytes with HIVenv 2-8 cells or HIV infected CD4+cells results in a lethal signal generated via interaction of HIV gp120/41 with the CD4 molecule of target T lymphocytes (Kowalski, 1991; Cohen, 1992; Hivroz, 1993; Heinkelein, 1995; Corbeil, 1996, incorporated herein by reference). The CD4+cells form syncytia, and undergo a process known as apoptosis or programmed cell death.

Research conducted in the areas of eukaryotic cell cycle control and apoptosis have found that the two events are closely linked. Furthermore, many enzymes and transcription factors that function in promoting cellular growth also appear to participate in cell death. These include c-Myc, p53, cyclin dependent kinases, and cyclin proteins, Bcl-2, and Bax. And as already mentioned, HIV-induced cytopathicity has also been shown to invoke alterations in the phosphorylation state and/or the expression of CDK1 (p34$^{cdc2}$) and cyclin B (Colten, 1992; Kolesnitchenko, 1995, incorporated herein by reference). Other stimuli that activate programmed cell death also produce aberrant expression and activation of the cyclin dependent kinases.

3. The Aryl Hydrocarbon Receptor

The Aryl Hydrocarbon (Ah) receptor is an intracellular cytosolic protein found in higher vertebrates in several epithelial tissues. The effects of Ah receptor ligands are known almost entirely in regards to their effects on P4501A1 induction, an enzyme system that metabolizes certain xenobiotics (Landers and Bunce, 1991, incorporated herein by reference). The Ah receptor was discovered by Poland and co-workers and studied first as a high affinity binding protein for aryl hydrocarbons of toxicological importance, most notably 2,3,7,8-tetrachlorodibenzo-p-dioxin (TCDD) (Poland et al., 1976 incorporated herein by reference).

Dioxins or dioxin-like compounds are environmental pollutants produced as unwanted byproducts of common industrial processes such as paper bleaching, incineration and chemical manufacturing.

Dioxins or dioxin-like compounds are a loosely defined family of organochlorine molecules with close structural and chemical similarities. Additionally, these compounds, by virtue of their similar structure and chemistry, share a common mechanism of toxicity. The prototypical dioxin, and the best studied, is 2,3,7,8 Tetrachlorodibenzo-P-Dioxin (sometimes called 2,3,7,8-TCDD or TCDD or dioxin). Besides 2,3,7,8 Tetrachlorodibenzo-P-Dioxin, this group of compounds include not only the dibenzo-p-dioxins, but also dibenzofurans, azobenzenes, dibenzo-ethers, certain polychlorinated biphenyls, certain polyaromatics and other compounds. Toxicity of these compounds is dependent on a planar, polyaromatic structure with lateral halogen substitutions.

The biochemical and physiological basis of dioxin toxicity has been the subject of intense scientific scrutiny. Animals vary in their susceptibility to dioxins and in their symptoms. In guinea pigs, as little as 600 ng per kg produces a lethal wasting syndrome. In humans, toxic responses to dioxin exposure include several proliferative aberrations such as hyperkerotinosis and hyperplasia. Despite much research in the area, the biochemical and physiological events that produce toxicity are poorly understood.

Although the ultimate physiological events that produce toxicity are poorly understood, it is generally agreed that toxicity of these chemically and structurally related dioxin-like compounds is due to their ability, by virtue of their chemical and structural properties, to bind to the intracellular Ah receptor. Although the ability of a compound to be a ligand of the Ah receptor is a requirement for dioxin-like toxicity, these compounds must also be able to promote transformation of the receptor to a DNA-binding form subsequent to ligand binding in order to be toxic. The transformation of the Ah receptor comprises a series of poorly understood events that include dissociation of the inactive receptor from a complex of proteins that include one or more molecules of the chaperonin HSP90, the formation of a new complex that includes HSP90-dissociated Ah receptor plus bound dioxin and the nuclear protein Aryl Hydrocarbon Nuclear Translocator (ARNT), and the binding of the Ah receptor/ARNT complex to specific DNA sequences.

These sequences, called Dioxin-Response Elements (DREs) or Xenobiotic-Response Elements (XREs), lie upstream of the promoter regions of certain genes, the most studied being the P4501A1gene. The binding of the transformed Ah receptor and associated protein(s) to the DREs enhance transcription of the associated genes. The inappropriate expression of these genes are thought to be the early events in the pleiotropic response to dioxins. It is fundamental that dioxins, in order to be toxic, must be able to both bind to the Ah receptor and transform it into an active form, and that this binding/transformation couplet is the central and only defined biochemical event in the toxic effects of dioxins.

Different dioxin-like compounds, although they share a common mechanism of toxicity, have different toxic potencies that can differ by several orders of magnitude. The toxicity of an unknown mixture of dioxin-like compounds can vary considerably depending on the identity and concentrations of the congeners present. Thus, the concept of Toxic Equivalency Factors (TEFs) and Toxic Equivalence (TEQs) have been advanced by some scientists. TEFs are the fractional toxicity of a dioxin-like compounds compared to the most toxic, prototypical 2,3,7,8-TCDD. Published TEFs are arbitrarily assigned values based on consensus toxicity's in the scientific literature. TEQs are the estimated toxic potential of a mixture of these compounds calculated by adding their respective TEFs with adjustment for their respective concentrations. TEFs and TEQs have been promoted by the EPA in order to facilitate their risk and hazard assessment of these compounds when they occur as mixtures.

The sequence of known events when an agonist or Ah ligand binds to the Ah receptor can be summarized as follows. The Ah receptor in the unbound state is found bound to the chaperonin HSP90 and another poorly understood protein or proteins (Perdew and Hollenback, 1990, incorporated herein by reference). Agonists of the Ah receptor such as TCDD, upon binding to the receptor, alter the receptor (commonly referred to as "transformation") so that the liganded Ah receptor separates from the chaperonin complex, translocates to the nucleus, binds to the ARNT protein, binds to specific DNA sequences upstream of the P4501A1 gene sequence as the Ah receptor: ARNT complex, and enhances transcription of P4501A1.

Antagonists and inhibitors of the Ah receptor have not been well-studied. Research interest has focused on potent, toxic agonists of the Ah receptor such as TCDD. Research interest on antagonists of the Ah receptor has focused on understanding the biochemistry of the Ah receptor, interactions among man-made toxins, and as inhibitors of estrogen-mediated gene expression. Known antagonists of the Ah-receptor include some flavone derivatives (Gasiewicz and Rucci, 1991; and Lu et al., 1995, both incorporated by reference) and synthetic aryl hydrocarbons (Merchant and Safe, 1995, incorporated herein by reference).

Ah receptor agonists and antagonists of plant and dietary origin are known (Kleman et al., 1994; Bjeldanes et al., 1991; and Jellinck et al., 1993, all incorporated herein by reference). Interestingly, these compounds are thought to be anti-carcinogens, tumor promoters, or both, however, mechanisms of action remain unknown.

The biochemical effects of agonists of the Ah receptor are generally thought to be Ah receptor-dependent, that is, the potency of the toxic response is proportional to their ability transform the Ah receptor (Wheelock et al., 1996 incorporated herein by reference), or induce P4501A1 (Zacharewski et al., 1989 incorporated herein by reference). However, the induction of P4501A1 itself is probably not connected with most of the physiological effects of Ah receptor ligands. Ah receptor ligands can act as anti-estrogenic tumor dependent agents by virtue of the ability of the Ah receptor: ARNT complex to interfere with estrogen receptor-mediated transcription. TCDD effects on both cellular proliferation, and apoptosis may occur via perturbation of intracellular signal transduction systems involved with cellular proliferation and apoptosis, as evidenced with by intracellular protein phosphorylation (Ma, 1992, incorporated herein by reference), induction of protein-tyrosine kinases, and cyclin dependent kinases (Ma and Babish, 1993 incorporated by reference).

The natural function of the Ah receptor is unknown, however, deletion of the Ah receptor results in liver abnormalities and immune system impairment. Furthermore, the identification of any endogenous ligand has remained elusive, and how Ah receptor-mediated signaling interacts with cell cycle and apoptotic control is poorly understood, and a direct connection has not been established.

4. Synergistic Effects with Other Compounds

The present invention concerns the identification of compounds useful in the treatment of cellular cytopathic changes, such as those caused by viral infection or some types of cancers. In that effort, the present application has focused on the use of compounds which have been found to be antagonists of the Ah receptor, capable of preventing the transformation of this receptor to its active form. As already discussed, the efficacy of Ah receptor antagonists has much to do with manipulation of certain proteins in the signal transduction pathways, whose consistent overexpression causes cytopathic changes in cells.

Along this line of investigation, it was believed that other compounds which had demonstrated the ability to inhibit cytopathic changes in cells could be used with Ah receptor antagonists in combinational therapy. This possibility of combinational therapy promised the potential to enhance the down-regulation of specific intracellular proteins thought responsible for observed cytopathic changes, such as CDK1, c-Mos, and cyclin B, thereby inhibiting the proliferation of cells demonstrating cytopathic changes. Combinational therapy would therefore act synergistically to enhance the efficacy of the overall therapy.

A specific compound extracted from the plant *Andrographis paniculata*, andrographolide, is known to have this type of pharmacological activity. This component of *Andrographis paniculata*, has been shown to have anti-HIV effects. Moreover, andrographolide has been shown to have anti-viral, anti-neoplastic and hepatoprotective properties. (See the document WO 96/17605, *Use of Andrographolide Compounds treat or prevent Pathogenicity of Diseases,* incorporated herein by reference). Therefore the impetus to use it in a combinational therapy was a strong one. Additionally, it has been found that while andrographolide has been shown to act on some of the same proteins, it does not bind the Ah receptor. This discovery, and the use of a combinational therapy with various Ah receptor antagonists, then provides for a broader and potentially more effective therapeutic intervention into viral infections generally, as well as AIDS, some cancers, and other pathological conditions than could be expected with each compound alone.

A tremendous advantage of finding compounds such as Ah receptor antagonists or Andrographolide derivatives with which to treat non-viral cellular targets, c-MOS and the downstream proteins CDK1 and cyclin B1, is that this mode of fighting pathological conditions, in addition to its synergistic effects, substantially eliminates the opportunity for viral mutation and alteration to affect the efficacy of the treatment. The implications of these findings are far reaching.

SUMMARY OF THE INVENTION

The present invention presents a novel method of treating a viral infection generally and an infection by the human immunodeficiency virus (HIV-1) specifically. The key to this treatment rests on a more complete understanding of intracellular mechanics and signal transduction. With the knowledge that a great many cellular conditions are caused through the derangement in the cell cycle machinery also comes the understanding that the discovery of compounds that affect this machinery, either alone or in combination, could have substantial therapeutic value. The Inventors, through experience and experimentation understood this and used this knowledge to discover a number of different compounds that are useful in the beneficial management or treatment of the said intracellular machinery. The focus in this patent is the Ah receptor and the use of compounds which act as agonists or antagonists of that receptor. By acting as agonists or antagonists the compounds exhibit their value as therapeutics through the perturbation of viral pathogenic signal transduction pathways. Many of the compounds found to have such activity are present in the claims of this application.

Antagonists of the Ah receptor are more likely candidates for treatment because the toxicity of such compounds is low. The efficacy of Ah receptor antagonists has much to do with manipulation of certain proteins in the signal transduction pathways, whose consistent overexpression causes cytopathic changes in cells. Moreover the identification of molecules affecting cellular targets, such as the Ah receptor, that also inhibit viral signal transduction are of great therapeutic potential since the activity of these molecules is not directed against the virus itself This targeting of cellular targets for therapy rather than viral targets prevents viral mutation from destroying or dulling the effectiveness of the disclosed therapy.

This discovery, and the use of secondary compounds such as Andrographolide or Quercetin in combinational therapy with various Ah receptor antagonists, then provides for a broader and potentially more effective therapeutic intervention into viral infections generally, as well as AIDS, some cancers, and other pathological conditions than could be expected with each compound alone. This is true because the effects of these separate compounds, though very significant on their own, are enhanced by use in combination. As disclosed herein the dosage requirements are generally lessened for the observance of a given effect—reducing potential toxicity. Since many of the secondary compounds work on other aspects of the cellular machinery, their use in combination allows more points in the signal transduction cascade to be controlled for the beneficial lessening of cytopathic, virally induced, changes in cellular activity.

BRIEF DESCRIPTION OF THE DRAWINGS

FIG. 1. Presents a model offering an abbreviated graphic explanation for T cell death by the HIV-1 virus.

FIG. 2. Shows the inhibition of cyclin B overexpression through the use of Herbimycin A.

FIG. 3. Shows the inhibition of cyclin B overexpression through the use of 2,3,7,8-Tetrachlorodibenzo-P-Dioxin (TCDD).

DETAILED DESCRIPTION

This invention pertains to the use of the aryl hydrocarbon (Ah) receptor protein complex as a drug target, which when bound to a ligand (e.g. agonist or antagonist) acts to reduce and/or inhibit the detrimental effect of viral infection. Specifically the compounds discovered to be effective in binding the Ah receptor also have the effect of inhibiting viral cytopathicity generally, and the T cell depletion (cytopathicity) that occurs from infection with the human immunodeficiency virus-1 (HIV) specifically. Also addressed in this application is the use of Ah receptor ligands in conjunction with other compounds to achieve synergistic effects in the treatment of cellular cytopathic events initiated by derangement's of signal transduction pathways.

Research conducted in the areas of apoptosis and cell cycle regulation have found that the two events are closely linked. Furthermore, many enzymes and transcription factors that function in promoting cellular growth also appear to participate in cell death. Such molecules include c-Myc, p53, cyclin dependent kinases (cdk's) and the cyclins, Bcl-2, and Bax. The activity of Ah receptor ligands has been examined to identify their role in viral induced cytopathicity, specifically HIV viral replication and associated T cell death. Our research has found that HIV-induced cytopathicity, as well cytopathic events that are a part of other viral infections, involve the hyperphosphorylation of CDK1, overexpression of cyclin B, and overexpression of the c-Mos protein kinase in transformed CD4+T cell lines, as well as in peripheral blood mononuclear cells.

With cell lines that demonstrated HIV-induced cytopathic cell signaling, the capability of various Ah receptor agonists and antagonists to mediate cellular signal transduction pathways, and thereby inhibit viral signal transduction, was assessed. This was performed utilizing T cell lines, exposed to Ah receptor agonists and antagonists, that express gp 120/41 on their cell surface (HIVenv 2-8 cells), which induced syncytia formation and cell death when co-cultured with CD4+T lymphocytes. It was found that all the compounds tested which had an affinity for the Ah receptor inhibited the overexpression of cyclin B as well as blocked the hyperphosphorylation of cdk1. This acted to lessen viral cytopathicity.

In this application it has been demonstrated that HIV gp 120/41 cytopathic signaling can be circumvented or degraded with Ah receptor agonists and antagonists. This process seeks a non-viral cellular target, the Ah receptor, with therapeutic potential for prevention of T cell depletion by HIV-1, because it substantially eliminates the opportunity for viral mutation and alteration to affect the efficacy of the treatment. The implications of these findings are far reaching. First, a cellular receptor molecule was identified which upon ligand binding can disrupt the viral signal transduction pathways initiated by virally infected cells. With infected CD4+T cells, the binding of a ligand to the Ah receptor has been shown, through experimentation, to inhibit the viral signal transduction generated by cells expressing the HIV envelope proteins gp 120/41. This discovery then provides for the therapeutic intervention into viral infections generally as well as the HIV-induced T cell depletion.

This therapeutic intervention may be augmented by the use of combinational therapy:, whereby more than one effective compound is used to treat a given condition or virally induced pathology. In the current application this type of therapy includes the use of various Ah receptor ligands in conjunction with another compound which has also been found to inhibit derangement of signal transduction pathways. This compound is the diterpene lactone andrographolide.

EXAMPLE 1

The Inhibition of HIV Envelope gp120/41-Induced Cytopathic Effects by Ah Receptor Agonists and Antagonists Ah receptor ligands were tested for the capacity to inhibit cytopathic changes in CD4+T cell lines following co-incubation with a T cell line (HIVenv 2-8) known to mimic HIV-induced cytopathic changes (syncytia formation) in vitro. The ability of each individual compound to inhibit syncytia formation and subsequent cell death was in general accordance with reported affinities for Ah receptor transformation to a DNA binding or transcriptionally active form from both human and rodent (mouse, rat, guinea pig) species (Wheelock et al., 1996). In addition, treatment yielded no obvious cytotoxicity to the cells. 2,3,7,8-Tetrachlorodibenzo-P-Dioxin (TCDD) was the most effective compound and strongest Ah receptor agonist with 3,3',4,4',5-pentachlorobiphenyl, 3,3',4,4'-tetrachlorobiphenyl and α-naphthoflavone exhibiting correspondingly weaker activity (e.g. required higher concentrations to protect against cytopathicity). Furthermore, α-naphthoflavone, a compound described to act as an Ah receptor antagonist by inhibiting TCDD-induced Ah receptor transformation to a DNA binding form, was also effective at inhibiting syncytia formation. A non-Ah receptor binding dioxin congener, 2-monochlorodibenzo-P-dioxin was incapable of blocking the cytopathic effect, demonstrating the essential role of interaction with the Ah receptor in the inhibition of HIV envelope gp120/41 induced T cell cytopathicity. This data then supports the view that the Ah receptor transformation to a DNA binding form is not required to inhibit HIV-1 gp120/41-induced syncytia formation and T cell death. Experimentation has been shown that the higher the affinity for interaction with the Ah receptor a compound displays, the more effective that compound would be for treating viral cytopathicity. Therapeutically speaking, the Ah receptor antagonists are far more appealing compounds in that their toxicity to a potential patient is many orders of magnitude lower than Ah receptor agonists such as TCDD (Merchant, 1995, incorporated herein by reference).

Materials and Methods

Sourcing of Ah Receptor Ligands: The Ah receptor ligands 2,3,7,8-Tetrachlorodibenzo-p-dioxin, 3,3',4,4',5-Pentachlorobiphenyl, 3,3',4,'4-Tetrachlorobiphenyl, and 2-Monochlorodibenzo-p-dioxin compounds were purchased from Accustandard (Cambridge, Mass.). α-naphthoflavone was purchased from Sigma (St. Louis, Mo.). Stock solutions of each compound were prepared by dissolution in DMSO at a 1000X concentration, i.e. the highest concentration tested was diluted by 1000-fold.

Bioassay Procedure: The cell lines utilized in the assay protocol include the following: HIVenv 2-2 (non-cytopathic), HIVenv 2-8 (cytopathic), Jurkat CD4+T cell line (clone E6-1), and SupT1. Cell lines were cultured in RPMI medium (Gibco, Grand Island, N.Y.) supplemented with L-glutamine (Sigma, St. Louis, Mo.) and 10% FBS-HI (Intergen). The Jurkat CD4+T cell line was obtained from American Type Culture Collection (Bethesda, Md.). All other cell lines were obtained from the National Institutes of Health. The HIVenv 2-2 or HIVenv 2-8 cells were plated with both CD4+T cell lines ($1\times10^3$ cells per cell line in 16 μL of media.) in a 96-well tissue culture plate containing 50 μL of media with compound to be tested yielding a final volume of approximately 100 μL. The plates were then gently shaken to ensure adequate mixing of the assay components. Cells were then co-cultured at 5% $CO_2$, 37C., and 95% humidity for 24 to 48 hours. The time points were chosen for the convenience, cytopathic changes become evident in the cell cultures used within a 2 to 4 hour period, becoming more and more prominent with time.

Another procedure which provides data similar to the Bioassay procedure just described allows for quantification of changes in the co-culture cells through an ELISA method, not as reliant on visual observation (see below).

Cyclin B ELISA procedure: The overexpression Cyclin B has become associated with HIVenv 2-8 cytopathicity. This biochemical response and it's inhibition by Ah receptor ligands has been assayed by ELISA. Following 24 hours of co-culture in 96 well microtiter tissue culture plates, the cells are washed 1X with PBS buffer and then lysed with 50 μL lysis buffer (50 mM Tris, 137 nM NaCl, 10% glycerol, 1% NP-40) with shaking at 4° C. for 30 minutes. Thirty microliters of the cell lysate were then transferred into Immulon 4™ ELISA strip plates and 70 μL of coating buffer (0.2M Borate pH 10.5) added to bring the final microtiter well volume to 100 μL The plates were then incubated at 37° C. for 1 hour to allow for coating. The plates are then washed 3X with 300 μl TBST (20 mM Tris, 150 mM NaCl, 0.05% Tween 20, pH 7.5), incubated with 125 μL of blocking solution for 5 minutes, washed 3X, incubated with horseradish peroxidase labeled anti-mouse IgG for 1 hour at room temperature, washed 3X, and then incubated with 100 μL TMB substrate for 30 minutes at room temperature. Stop solution (2.5M sulfuric acid, 100 μL) was then added to prevent further color development and the plate was read at an optical density of 450 nm.

Data Reduction for this ELISA: HIVenv 2-2 co-culture ELISA values are used as the background for HIVenv 2-8 co-culture values. Dose responses are then plotted with dose along the x-axis and the background corrected optical density values on the y-axis.

Positive and Negative Controls: The use of the HIVenv 2-2 cell line serves as a negative control for induction of cytopathicity. The tyrosine kinase inhibitor herbimycin A was previously shown to block the HIVenv 2-8 induced cytopathic effect and functioned as a positive control.

Determination of Viable Cell Counts: Estimates of cell viability were made by visual observation and trypan blue dye exclusion.

Biochemical Effects: The cytopathic effect induced by HIV and the tissue culture system employed here resulted in dramatic biochemical changes within the affected cells. The expression of the protein kinase c-Mos was induced in addition to alterations in cell cycle (CDK1, cyclin B) and apoptotic (Bcl-2 and Bax) protein concentrations and phosphorylation status. CDK1 became hyperphosphorylated whereas cyclin B, Bcl-2, and Bax expression were elevated. Assay for these biochemical changes was performed by western blot analysis using equal amounts of cell lysate proteins derived from cells cultured with the respective Ah receptor ligands. Responses were quantified by scanning densitometry.

Interpretation of the Test: A positive response was defined as a dose-related decrease in syncytia formation in excess of 50% compared to HIVenv 2-8 co-cultures alone. Calculation of median effective doses was estimated by visual observation and by quantification of syncitia in 10X power microscope fields.

Results

Ligands of the aryl hydrocarbon (Ah) receptor produced dose-dependent inhibition of cell death in the HIVenv 2-8 co-cultures. The inhibition of HIVenv 2-8-mediated syncytia formation and cell death occurred in the absence of cytotoxicity from the ligands themselves. The visual inhibition of cell death is demonstrated graphically in FIGS. 2 and 3, and can also be seen in tabular form throughout this application. Visual quantification of syncytia on 10X microscope fields (FIG. 2) confirmed the dose-response patterns from which an estimated concentration for 50% inhibition (IC50) of cytopathicity was calculated. The estimated IC50 value for each Ah receptor ligand is found in Table 1.

Biochemically, Ah receptor ligands prevented both the hyperphosphorylation of CDK1 and cyclin B overexpression. CDK1 hyperphosphorylation and cyclin B overexpression have been shown to correlate with cell death. (Cotten et al., Proc. Natl. Acad. Sci. 1995). The prevention of cytopathicity is affected through ligands to the Ah receptor by activating signaling pathways which interfere with the pathways initiated by gp120/41 interaction with CD4 at the cell surface which initiates the hyperphosphorylation of CDK1 and cyclin B overexpression. The results for TCDD and substituted furans using from western blotting are as shown in Table 2.

This example indicates that certain ligands of the Ah receptor are capable of blocking the cytopathic signaling to CD4+T cells induced by the HIV gp120/41 interaction with the CD4 surface molecule. Biochemically this was shown to be due in part to prevention of CDK1 hyperphosphorylation and cyclin B over expression.

TABLE 1

Estimated IC50 Values of Inhibition of HIV-Induced Cytopathicity by Ah Receptor Ligands.

| Ah Receptor Ligand | Estimated IC50 (Syncitia Quantification) |
|---|---|
| 2,3,7,8-TCDD | 2 nM |
| 3,3',4,4'-TCB | 35 nM |
| 2,3,7,8-TCDF | 80 nM |
| 3,3',4,4',5-PCB | 100 nM |
| α-naphthoflavone | 350 nM |
| 2-MCDD | No Inhibition Observed |
| 1,2,3,4,7,8-HCDD | No Inhibition Observed |
| Herbimycin A (Non Ah Receptor Control) | 750 nM (.43 μM) (Positive Control) |
| 6-t-butyl,1,3,8-trichlorodibenzofuran | 1500 nM |
| 6-nitro 1,3,8-trichlorodibenzofuran | 500 nM |
| 6-ethyl,1,3,8-trichlorodibenzofuran | 1000 nM |
| 6-cyclohexyl,1,3,8-trichlorodibenzofuran | 500 nM |
| 6-isopropyl,1,3,8-trichlorodibenzofuran | 100 nM |
| 6-methyl,1,3,8-trichlorodibenzofuran | 200 nM |
| 6-propyl,1,3,8-trichlorodibenzofuran | 500 nM |
| 1-bromo,6-methyl,3,8-dichlorodibenzofuran | 100 nM |
| 6-butyl,1,3,8-trichlorodibenzofuran | 1500 nM |

6-t-butyl 1,3,8-trichlorodibenzofuran 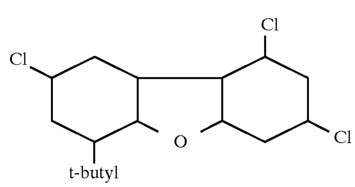 6-nitro,1,3,8-dichlorobenzofuran 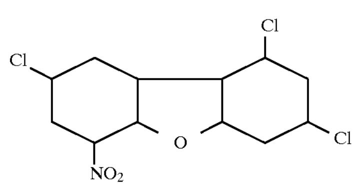 6-ethyl,1,3,8-trichlorodibenzofuran 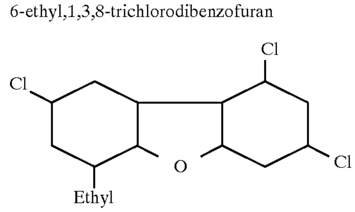 -continued 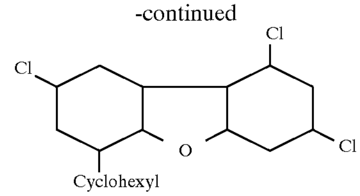 6-cyclohexyl,1,3,8-trichlorodibenzofuran 6-Isopropyl,1,3,8-tricholorbenzofuran 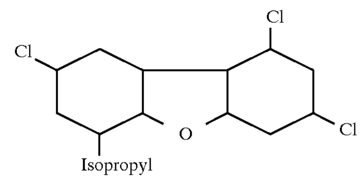 6-methyl,1,3,8-trichlorodibenzofuran 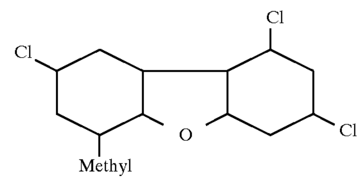 6-propyl,1,3,8-trichlorodibenzofuran 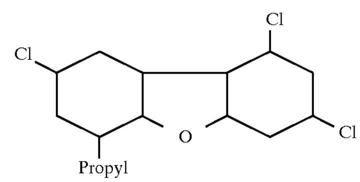 1-bromo,6-methyl,3,8-dichlorobenzofuran 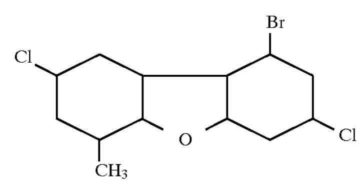 6-butyl,1,3,8-trichlorodibenzofuran 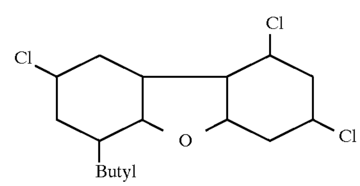 Dibenzofuran Compounds of Interest The chemical structures of the dibenzofuran compounds mentioned in Table 1.

TABLE 2

Inhibition of Cyclin B Overexpression and CDK1 Hyperphosphorylation By Ah Receptor.

| Treatment/Culture | Cyclin B | CDK1 Phosphorylation |
|---|---|---|
| 2-2 Co-culture | 10.14 ± 2.3 | 10.41 ± 3.8 |
| 2-8 Co-culture | 61.88 ± 10.7 | 44.27 ± 11.5 |

TABLE 2-continued

Inhibition of Cyclin B Overexpression and CDK1
Hyperphosphorylation By Ah Receptor.

| Treatment/Culture | Cyclin B | CDK1 Phosphorylation |
|---|---|---|
| TCDD | 9.32 ± 2.7 | 11.13 ± 3.3 |
| 6-alkyl substituted Furans | 10.19 ± 3.3 | 11.33 ± 2.1 |

Data from Table 2 represents the mean ± standard error of scanning densitometric units (n=5 or 6 individual scans from separate experiments). Doses used were as follows: TCDD, 10 nM; Substituted Furans (6-nitro 1,3,8-trichlorodibenzofuran; 6-isopropyl, 1,3,8-trichlorodibenzofuran; 6-methyl, 1,3,8-trichlorodibenzofuran; 1-bromo, 6-methyl, 3,8-dichlorodibenzofuran), 2 μM. All four alkyl substituted furan compounds that were tested yielded approximately equivalent responses so their responses were combined.

EXAMPLE 2

Traditional Chinese Medicine (TCM) Extracts were Chosen from a Group of Extracts Not Previously Tested for the Ability to Inhibit Syncitia Formation

Summary

Cytosol was prepared as described in methods and treated with TCDD, DMSO or TCM extract to make 1) 0.5 nM TCDD, 2) 0.1% DMSO, or 3) 500 μg/mL TCM extract, respectively. The treated cytosol was serially diluted in a neutravidin-coated ELISA plate (Pierce, Rockford, Ill.). The extracts were diluted into DMSO treated cytosol to give additional concentrations of 250, 125, and 62.5 μg/mL TCM extract. To treat for Ah receptor agonist activity, extracts were diluted in 0.5 nM TCDD treated cytosol to 250, 125, and 62.5 μg/mL of TCM extracts.

Materials and Methods

Reagents for Ah Receptor Transformation Assay

Preparing Guinea Pig Cytosol

The method and materials for preparing the Guinea pig cytosol are described below. Guinea pig cytosol is the source of the inactive Ah receptor and ARNT, HEDG buffer was composed of 25 mM HEPES (N-2(2-Hydroxyethyl)piperazine-N'-(2-ethansulfonic acid) Sodium salt), 1.5 mM EDTA (Ethylenediamine-tetraacetic acid Tetrasodium salt), 1 mM DTT (DL-Dithiothreitol), 10% glycerol, pH 7.6. Perfusion buffer was HEDG plus 1.15% (w/v) KCl (potassium chloride). Buffers were chilled on ice before use.

Male Hartley Guinea pigs weighing 300–350 g were purchased from Cornell Research Animal Resources, Cornell University, Ithaca, N.Y. Guinea pigs were anaesthetized and killed with carbon dioxide. Livers were perfused in situ with 100 mL ice-cold perfusion buffer, excised, trimmed of connective tissue, poorly perfused liver and gall bladder and weighed. The liver was minced and five mL of ice-cold HEDG per gram liver were added and the whole homogenized in a 50 mL homogenizer with teflon pestle at 200 rpm for a total of seven strokes. Crude homogenate was centrifuged at 12,500 RPM in 50 mL tubes in a JA17 rotor in a Beckman J2-MI preparative centrifuge at 4° C. for 20 minutes.

Post-centrifugation lipid was again removed by aspiration and discarded. The supernatant liquid was decanted and the pellet was discarded. Pooled supernatant fractions were centrifuged for 60 min. at 4° C. at 37,000 RPM in 25 mL ultracentrifuge tubes in a 70 TI rotor in a Beckman ultracentrifuge model L8-70M.

Lipid was again removed by aspiration and the supernatant fractions were decanted and pooled. Supernatant fractions were aliquoted into 10 mL aliquots and frozen at −80° C. until used.

DNA synthesis and hybridization: DRE oligonucleotides were synthesized under contract by Midland DNA or the Genosys corporation and had the following sequences:

SEQ ID 1- DRE-D: 5'-GAT CCG GAG TTG CGT GAG AAG AGC CA-3'

SEQ ID 2- B-ERD: BIOTIN-5'-TGG CTC TTC TCA CGC AAC TCC GGA TC-3'

Oligonucleotides were dissolved in MOPS/EDTA buffer (25 mM MOPS, 0.2 mM EDTA, pH 7.6) to a concentration of 0.5 nmol per mL. For hybridization, equal volumes of B-DRE and ERD-D were mixed in a 1.5 mL microfuge tube and placed for 5 min in 350 mL water contained in a 1L beaker maintained at 90° C. After 5 min the entire beaker was placed in a water bath for 4 hours maintained at 37° C. The hybridized DRE was diluted 10-fold with MOPS/EDTA buffer and stored frozen −80° C. in 20 μL aliquots.

Neutravidin-coated 96 well ELISA plates were obtained from Pierce Chemical Co, Rockford, Ill. Alternatively, neutravidin-coated ELISA plates were made using the following procedure:

Neutravidin (Pierce) was dissolved to 2 mg/mL in PBS plus 0.02% sodium azide. The neutravidin was diluted to 20 μg/mL in 0.1 MES buffer, pH 6.0 and pipetted into Immunlon 4 ELISA plates at 200 μL per well. The plates were incubated for 19 hours at 4° C., washed 3 times with 400 μL TBS plus 0.02% Tween 20 per well per wash. Four hundred μL 1% BSA in TBS was added per well and the ELISA plates incubated 1 hour at RT with gentle rocking. The plates were washed again and 400 μL StabilCoat (BSI corp., Eden Prairie, Minn.) was added per well and incubated for 30 seconds. The StabilCoat was removed and the plates were lyophilized overnight.

anti-ARNT

Anti-ARNT #30-3B is a polyclonal affinity purified antibody to recombinant aa318-773 of mouse ARNT. It was a gift of Dr. Alan Poland and has been described by him. (Pollenz, R. S. et al., A Mol. Pharmacol. 45:428–438, 1994 incorporated herein by reference). The aryl hydrocarbon receptor and aryl hydrocarbon receptor nuclear translocator protein show distinct subcellular localization's in Hepa 1c1c7 cells by microscopy. Concentration of anti-ARNT stock was 110 μg/mL. The working dilution of anti-ARNT was 1:400 (50 L in 20 mL) in TBS plus 0.02% Tween 20 plus 0.1% bovine serum albumin.

anti Rabbit IgG alkaline phosphatase

Anti-Rabbit IgG alkaline phosphatase was obtained from Sigma Chemical Co., (St. Louis, Mo.). The working dilution of anti Rabbit IgG alkaline phosphatase was 1:4000 (5 μL in 20 mL) in TBS plus 0.02% Tween 20 plus 0.1% bovine serum albumin.

Diethanolamine buffer was prepared by dissolving 0.4 g Magnesium chloride hexahydrate, 0.8 g 2-chloroacetmide, 338 mL diethanolamine in 2.5 L deionized water, adjusting pH to 9.8 with concentrated HCl, and adjusting volume to 4 liters.

PNPP stock was prepared fresh by dissolving two 15 mg tablets of para-nitro phenyl phosphate (Sigma, St. Louis, Mo.) in 20 mL diethanolamine buffer.

Screening of TCM extracts for ability to induce or inhibit Ah receptor transformation.

Cytosol was prepared as described above. Ten mL aliquots of cytosol were thawed and pooled, generally 20 mL per ELISA plate. For each 20 mL of cytosol, 10 μL of thawed DRE stock and 1 mL HEDG in 4M NaCl were added.

Treatment of cytosol:

Diluent for TCDD dose response, diluent for extracts (detection of agonists), and negative control: The cytosol is treated with 1 μL DMSO per 1 mL cytosol (−).

1 nM TCDD treated, positive control. The cytosol is treated with 1 μL of 1 μM TCDD per 1 mL cytosol DMSO treated, negative control: the cytosol is treated with 1 μL DMSO per 1 mL cytosol. DMSO diluent for detection of agonists: the cytosol is treated with μL DMSO per 1 mL cytosol. (1 nm final concentration of TCDD).

0.5 nM TCDD Diluent for extracts (detection of antagonists): The cytosol is treated with 1 μl of 1 μM TCDD per 2 mL cytosol (0.5 nm).

500 μg/mL extracts (detection of agonists): 1 μL test extract (500 mg/mL in DMSO) in 1 mL cytosol (500 μg/mL final concentration of extract in cytosol).

500 μg/mL extracts (detection of antagonists): 1 μL of test extract (500 mg/mL in DMSO) in 1 mL 0.5 nM TCDD-treated cytosol (500 μg/mL final concentration of extract in cytosol).

Serial dilution's of the extracts and/or TCDD treated cytosol into DMSO-treated cytosol are done as required by the experiment and are described in the examples.

Performance of the ELISA

The ELISA plate containing the treated cytosol is incubated with gentle rocking for 2 hours at 30° C. to allow the transformation of Ah receptor, binding of Ah receptor with ARNT, and binding of the Ah receptor/ARNT complex to the biotinylated DRE, and binding of the biotinylated DRE to the neutravidin bound to the ELISA plate.

After 2 hours the plate is washed 3 times with 400 μL TBS plus 0.02% Tween 20 per well per wash and 200 μL of the working dilution of anti-ARNT added to all wells. The plate is again incubated with gentle rocking at 30° C. for 1 hour. After 1 hour the plate is washed as before and a working dilution (1:4000) of anti-rabbit/alkaline phosphatase conjugate is added to all wells. The plate is incubated for a further 1 hour at 30° C. with gentle rocking and then washed as before. PNPP stock is added to each well (200 μL) and the plate is incubated for 1 hour at 30° C., at which time it is read at 405 nm in an ELISA plate reader and the milli O.D.'s of the wells are recorded.

TABLE 3

Extracts Tested for Ah receptor agonist activity. Values represent milli O.D. measurements by Ah-immunoassay. Extracts were diluted in DMSO, absent TCDD

| Extract No. | Extract Concentration in μg/mL | | | |
|---|---|---|---|---|
| | 62.5 | 125 | 250 | 500 |
| #379 | 142.5 | 193 | 210 | 147.5 |
| #452 | 30.5 | 20 | 34.5 | 51 |
| #539 | 16.5 | 31 | 64 | 95 |
| #549 | 52 | 97 | 151 | 167.5 |
| #557 | 79 | 91.5 | 93.5 | 90.5 |
| #558 | 22 | 29.5 | 53 | 39.5 |
| #562 | 33.5 | 25.5 | −10.5 | −39.5 |
| #564 | 19 | 20 | 25 | 9.5 |

TABLE 4

Ability of TCM extracts to inhibit transformation of the Ah receptor in the presence of 0.5 nM TCDD. Values represent milli O.D. end points of Ah immunoassay. Extracts were diluted in 0.5 nm TCDD diluent (i.e., in the presence of TCDD).

| Extract No. | Extract Concentration in μg/mL | | | |
|---|---|---|---|---|
| | 62.5 | 125 | 250 | 500 |
| 379 | 1940 | 1642 | 1324 | 847 |
| 452 | 1984 | 1935 | 1918 | 1722 |
| 539 | 2060 | 1931 | 1725 | 1218 |
| 549 | 1992 | 1834 | 1478 | 883 |
| 557 | 631.5 | 564 | 492 | 328.5 |
| 558 | 1803 | 1454 | 905 | 229.5 |
| 562 | 1628 | 519 | −167 | −276 |
| 564 | 1419 | 886 | 346 | −110 |

Table 3 shows the response of the Ah receptor to the extracts. None of the extracts showed ability to transform the Ah receptor. Table 4 shows the ability of extracts to inhibit transformation. All extracts except #452 showed ability to inhibit transformation, with variable dose responses. Extract #557 strongly inhibited transformation even at the lowest dose used (62.5 μg/mL), while extracts #562, 564, 549, 558, 539 and 379 showed responses intermediate between #452 and #557. These preliminary results showed that the assay was capable of detecting inhibition of Ah receptor transformation by herbal extracts. Additional preliminary conclusions were that transformation of the Ah receptor by herbal extracts was more rare than inhibition of transformation, and that different herbal extracts exhibited different dose-response ranges and shapes, suggesting different mechanisms of action. The near ubiquity of inhibition at extremely high doses suggested the possibility of non-specific effects such as a poisoning effect, or an effect caused by a common plant material. Of the eight extracts tested, only #557 was judged to have a discriminating, unusual effect.

EXAMPLE 3

TCM Extracts Are Tested for Ability to Transform the Ah Receptor or Inhibit Transformation of the Ah Receptor Summary TCM extracts were chosen from a group of extracts tested for ability to inhibit syncitia formation.

Cytosol was prepared as described in methods and treated with TCDD, DMSO or TCM extract to make (1) 0.5 nM TCDD, (2) 0.1% DMSO, or (3) 500 μg/mL TCM extract, respectively. The treated cytosols were serially diluted in a neutravidin-coated ELISA plate prepared according to Methods. The extracts were diluted into DMSO-treated or 0.5 nM TCDD-treated cytosol to give additional concentrations of 250, 125, 62.5, 31.2 and 15.6 μg/mL TCM extract.

Cytosol transformation and ELISA development were as described in Example 2

Table 5 shows the ability of the extracts to transform the receptor. Two of thirteen extracts, #158 and 193, showed ability to transform the Ah receptor, with #158 being the stronger of the two. Table 6 shows the ability of test compounds to inhibit Ah receptor transformation. Seven (#511, 149, 40, 46, 158, 91) extracts showed ability to inhibit transformation at some dose but only #522 and 91 inhibited transformation at the lowest doses tried. Based on these results and the other data from Example 3 the preferred initial screening is composed of extracts at a dose of 500 µg/mL in prepared cytosol to screen for transformation (agonists) and at a dose of 15.6 µg/mL in prepared cytosol +0.5 nM TCDD to screen for inhibition. Inhibition of transformation at high doses was common, non-selective and possibly prone to artifacts. In contrast, screening for transformation at high doses and inhibition at low doses appeared more selective and discriminating.

TABLE 5

Ability of TCM extracts to transform the Ah receptor to a DRE/ARNT binding form. Data represents milli O.D. endpoint of the Ah-immunoassay.

| | Extract Concentration in µg/mL | | | | | |
|---|---|---|---|---|---|---|
| Extract No. | 15.63 | 31.25 | 62.5 | 125 | 250 | 500 |
| 30 | 11 | 25 | 42.5 | 61 | 103.5 | 157 |
| 40 | 87.5 | 89 | 127 | 177 | 282 | 341 |
| 46 | 60 | 57.5 | 66.5 | 81.5 | 99 | 82.5 |
| 91 | 95.5 | 88.5 | 116 | 112 | 67.5 | 12.5 |
| 149 | 41 | 31 | 55 | 70.5 | 100.5 | 99 |
| 158 | 77.5 | 237.5 | 411 | 534.5 | 513 | 701.5 |
| 193 | 76 | 81.5 | 144.5 | 216.5 | 362 | 497.5 |
| 458 | 16 | 8 | 28.5 | 27 | 31.5 | 27 |
| 510 | 23.5 | 2 | 18.5 | 23 | 40.5 | 71.5 |
| 511 | 29 | 25 | 47 | 76 | 120 | 77.5 |
| 522 | 36.5 | 14 | 25.5 | 24.5 | 27 | 28 |
| 529 | 31 | 36 | 68 | 82 | 73.5 | 23.5 |
| 530 | 18 | 16 | 42 | 56 | 94 | 118 |

TABLE 6

Ability of TCM extracts to inhibit Ah receptor transformation in the presence of 0.5 nM TCDD. Data represents milli O.D. endpoint of Ah-immunoassay. Extracts were diluted in DMSO diluent.

| | Extract Concentration in µg/mL | | | | | |
|---|---|---|---|---|---|---|
| Extract No. | 15.63 | 31.25 | 62.5 | 125 | 250 | 500 |
| 30 | 1449 | 1403 | 1527 | 1331 | 1166 | 650 |
| 40 | 1550 | 1544 | 1417 | 1245 | 998 | 582.5 |
| 46 | 1406 | 1282 | 1030 | 694.5 | 356.5 | 88.5 |
| 91 | 900.5 | 682 | 506 | 318.5 | 126.5 | 4 |
| 149 | 1330 | 1263 | 1054 | 740.5 | 358.5 | 97 |
| 158 | 1423 | 1438 | 1420 | 1406 | 1343 | 961.5 |
| 193 | 1566 | 1585 | 1565 | 1532 | 1455 | 947.5 |
| 458 | 1421 | 1375 | 1393 | 1323 | 1250 | 888.5 |
| 510 | 1403 | 1402 | 1408 | 1410 | 1388 | 1107 |
| 511 | 1440 | 1391 | 1233 | 948 | 477 | 6 |
| 522 | 1062 | 833 | 582.5 | 346.5 | 160.5 | 10.5 |
| 529 | 1368 | 1336 | 1204 | 922.5 | 492.5 | 103 |
| 530 | 1394 | 1326 | 1282 | 1122 | 849 | 434 |

EXAMPLE 4

Furan Compounds Tested for Their Ability to Inhibit HIV-Induced Cytopathicity by Acting as an Ah Receptor Ligand Summary Several dibenzofuran compounds were tested for the capacity to inhibit cytopathic changes in CD4+T cell lines using the HIV co-culture assay described in Example 1 above. This process of co-incubation with a T cell line (HIVenv 2-8) is known to mimic HIV-induced cytopathic changes (syncytia formation) in vitro. The ability of each individual compound to inhibit syncytia formation and subsequent cell death is detailed in Table 1 above. The compound, 1-bromo, 6-methyl, 3,8-dichlorodibenzofuran, was the most effective compound and strongest Ah receptor antagonist with 6-nitro 1,3,8-trichlorodibenzofuran, and 6-isopropyl, 1,3,8-trichlorodibenzofuran exhibiting slightly less antagonistic activity (e.g. required higher concentrations to protect against cytopathicity). The effective antagonism of the dibenzofuran compounds presented in Table 1 demonstrates the essential role of interaction with the Ah receptor in the degradation of viral induced cytopathicity generally and the inhibition of HIV envelope gp120/41 induced T cell cytopathicity specifically. As in Example 1 the data indicates that the Ah receptor transformation to a DNA binding form (Merchant, 1995) is not required to inhibit HIV-1 gp120/41-induced syncytia formation and T cell death.

The higher the affinity for interaction with the Ah receptor a compound displays, the more effective that compound would be for treating viral cytopathicity. Compounds that can act as Ah receptor antagonists are far more appealing compounds in that their toxicity to a patient has been shown to be tremendously lower than Ah receptor agonists such as TCDD (Merchant, 1995).

Materials and Methods

The Materials and Methods used in the testing of the various dibenzofuran compounds were the same as those used in Example 1 above. This includes the use of the same controls, cell lines, and assay procedures.

Interpretation of the Test: A positive response was defined as a dose-related decrease in syncytia formation in excess of 50% compared to HIVenv 2-8 co-cultures alone. Calculation of median effective doses was estimated by visual observation and by quantification of syncitia in 10X power microscope fields. Another procedure which provides data similar to the Bioassay procedure just described allows for quantification of changes in the co-culture cells through an ELISA method, not as reliant on visual observation.

Results

Figure 2:
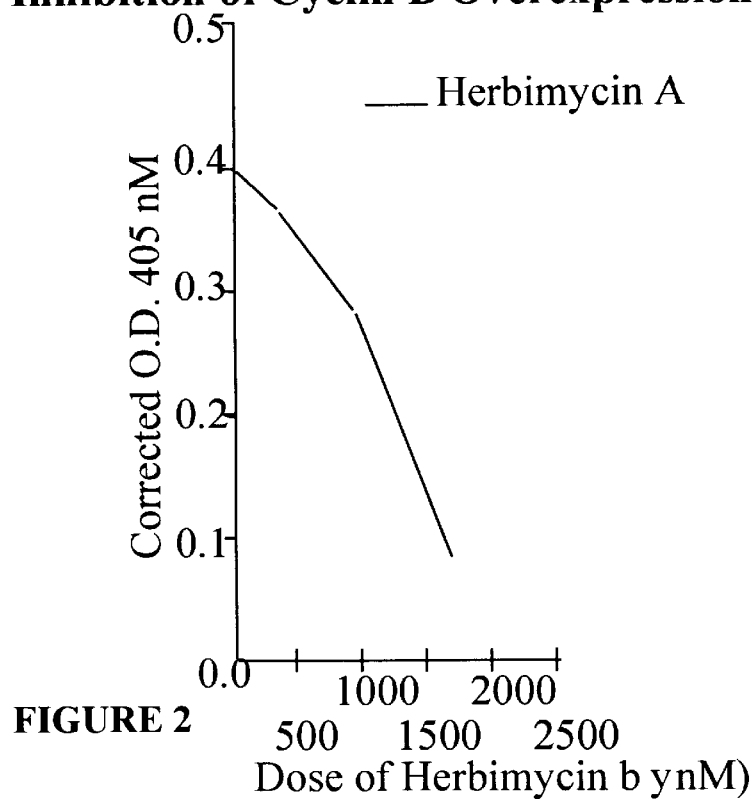
Figure 3:
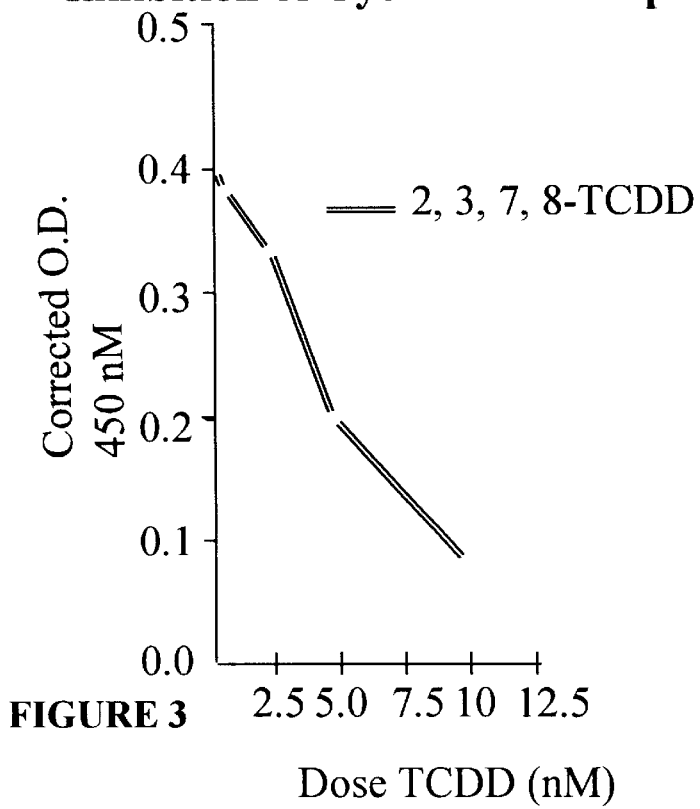

Visual quantification of syncytia on 10X microscope fields (FIG. 2) revealed dose-response patterns from which an estimated concentration for 50% inhibition (IC50) of cytopathicity was calculated. The estimated IC50 value for each Ah receptor ligand is found in Table 1.

Biochemically, the dibenzofuran compounds used prevented both the hyperphosphorylation of CDK1 and cyclin B overexpression. CDK1 hyperphosphorylation and cyclin B overexpression have been shown to correlate with cell death. The prevention of cytopathicity is affected through ligands to the Ah receptor by activating signaling pathways which interfere with the pathways initiated by gp120/41 interaction with CD4 at the cell surface which initiates the hyperphosphorylation of CDK1 and cyclin B overexpression. The specific signal pathway affected, and how it blocks cytopathic changes, is however, unknown.

This example indicates that certain ligands of the Ah receptor are capable of blocking the cytopathic signaling induced by viral activity in infected cells. Biochemically this was shown to be due in part to prevention of CDK1 hyperphosphorylation and cyclin B overexpression.

EXAMPLE 5

The Use of α-Naphthoflavone as an Agonist/ Antagonist of the Ah Receptor

Summary

α-naphthoflavone, a known partial agonist and antagonist of the Ah receptor, was tested for its ability to either transform the Ah receptor or to inhibit this transformation. The results were found using the ELISA assay for transformed Ah receptor as described in Example 2.

Cytosol was prepared as described in methods and treated with TCDD, DMSO or α-naphthoflavone to make (1) 0.5 nM TCDD, (2) 0.1% DMSO, or (3) 500 mM α-naphthoflavone respectively. The treated cytosols were serially diluted in a neutravidin-coated ELISA plate prepared according to Example 2. The 500 mM α-naphthoflavone in cytosol or 0.5 nM TCDD in cytosol was diluted into DMSO-treated or cytosol plus 0.5 nM TCDD to give additional concentrations of 250, 125, 62.5, 31.2 and 15.6 and 7.8 μM α-naphthoflavone in cytosol or cytosol plus 0.5 nM TCDD. Cytosol transformation and ELISA development were as described in Example 2.

Cytosol transformation and ELISA development were as described in Example 2

As table 7 demonstrates, α-naphthoflavone is a very weak agonist of the Ah receptor. Only the highest doses showed any response above background and the highest does tried 500 μM, did not reach the EC50 of TCDD (0.5 nM TCDD). α-naphthoflavone was a more potent antagonist of the Ah receptor, inhibiting the activity of 0.5 nM TCDD effectively in the experimental dose range. The IC50 of α-naphthoflavone was estimated at 18.6 μM. Data accumulation was accomplished through at 405 nm in an ELISA plate reader, for more information on this method please see Example 2. These results, as seen in the table below, show that the assay is capable of detecting antagonists of the Ah receptor. (Gasiewicz, T. A. and G. Rucci., Mol. Pharm., 1991 incorporated herein by reference).

TABLE 7

| | Concentration of α-Naphthoflavone | | | | | | |
|---|---|---|---|---|---|---|---|
| | 7.81 μM | 15.63 μM | 31.25 μM | 62.5 μM | 125 μM | 250 μM | 500 μM |
| No TCDD Added | 85 | 10 | 20 | 31.5 | 77.5 | 149.5 | 263 |
| Plus 0.5 nM TCDD | 735 | 458 | 338 | 248 | 296 | 279 | 308.5 |

The data in Table 7 above, shows that the α-naphthoflavone is a very weak agonist of the Ah receptor. In Table 6 only the highest doses showed any response above background and the highest dose tried, 500 μM, did not reach the EC50 of TCDD (0.5 nM TCDD). Alpha-naphthoflavone was a more potent antagonist of the Ah receptor, inhibiting the activity of 0.5 nM TCDD effectively in the dose range tried. The IC50 of α-naphthoflavone was estimated at 18.6 μM. These results show that the assay, as fully detailed in Example 2, is capable of detecting antagonists of the Ah receptor.

EXAMPLE 6

Relative Ah Receptor Antagonist Potency of TCM Extracts

TCM extracts were tested for their ability to inhibit the transformation of the Ah receptor. As seen in Table 8, the results indicate that there is a wide range of doses required to inhibit the transformation of the Ah receptor by 50% (C50). The assay used can discriminate antagonist potencies up to 500 μg/mL. Thus, an arbitrary discriminating dose can be chosen, such as 50 μg/mL, or 250 μg/mL, and then used to select a desired percentage of positives, the percentage of positives being determined by the discriminating dose chosen. Extracts can be screened at this one dose and defined as positive if the mini O.D. of the extract at that dose is below one-half of the response of 0.5 nM TCDD. Thus, it can be seen that by utilizing the rapid, high capacity ELISA format of the Ah-immunoassay large numbers of extracts, test compounds, or chromatography fractions can be readily screened for Ah receptor activity and the most active extracts, compounds, or fractions can be rapidly identified.

TABLE 8

Estimated IC50 Values of Inhibition of Transformation of Ah Receptor by TCM Extracts
Concentration in μg/mL

| Extract | IC50 |
|---|---|
| 91 | 25 |
| 557 | 32 |
| 522 | 40 |
| 562 | 100 |
| 149 | 115 |
| 564 | 126 |
| 511 | 162 |
| 529 | 162 |
| 558 | 251 |
| 530 | 295 |
| 30 | 427 |
| 379 | 457 |
| 549 | 501 |
| 158 | >500 |
| 193 | >500 |
| 452 | >500 |
| 458 | >500 |
| 510 | >500 |
| 539 | >500 |

Table 8 shows calculated IC50's for the extracts tested, ranked according to potency.

EXAMPLE 7

Extracts with High Ah-Receptor Antagonist Activity Exhibit High Activity in Inhibition of HIV Cytopathicity A method to screen extracts with high Ah-receptor and/or high inhibition of HIV cytopathicity was determined. The screening process involved selecting a discriminating range to determine Ah receptor antagonist activity. The range chosen was between 0–500 μg/mL and extracts with IC50's below 250 μg/mL were arbitrarily chosen as positives, Table 8 shows the extracts tested. The functional range of the HIV cytopathicity assay was 0–10 μg/mL and extracts with IC50's of less than 5 μg/mL were arbitrarily chosen as positives in this assay. Extracts were branded as double positives (PP) if they worked as antagonists of both the Ah and HIV cytopathicity. The extracts were branded as partial positives if they acted as antagonists of either the Ah receptor only (PN), or HIV cytopathicity only (NP). If they did not act as antagonists to either the Ah receptor or HIV cytopathicity then they were considered double negatives (NN), as shown in Table 10. The cross-product ratio, (PP× NN)/(PN×NP), yielded a value of 8.4 showing a strong correlation between an extract's ability to inhibit HIV cytopathicity and the same extracts ability to act as an Ah receptor antagonist.

TABLE 9

IC50's of Ah receptor Antagonists vs. IC50's in HIV Syncitia Formation

| A EXTRACT | B IC50 (Ah) | C IC50 (Syn) | D POS (Ah) | E POS (Syn) |
|---|---|---|---|---|
| 91 | 25 | 0.94 | yes | yes |
| 557 | 32 | 0.3 | yes | yes |
| 522 | 40 | 0.25 | yes | yes |
| 562 | 100 | 6 | yes | no |
| 149 | 115 | 1.5 | yes | yes |
| 564 | 126 | 0.7 | yes | yes |
| 511 | 162 | 0.2 | yes | yes |
| 529 | 162 | 0.35 | yes | yes |
| 558 | 251 | 0.8 | no | yes |
| 530 | 295 | 10 | no | no |
| 30 | 426 | 10 | no | no |
| 379 | 457 | 9 | no | no |
| 549 | 500 | 0.25 | no | yes |
| 158 | 500 | 1.8 | no | yes |
| 336 | 500 | 0.5 | no | yes |
| 452 | 500 | 1.25 | no | yes |
| 458 | 500 | 25 | no | no |
| 510 | 500 | 7.5 | no | no |
| 539 | 500 | 5 | no | no |

Column A: Extract Code
Column B: Ah receptor antagonist IC50 in $\mu$g/mL. Values equal or greater than 500 listed as 500.
Column C: = Inhibition of syncitia formation in $\mu$g/mL. Values equal or greater than 10 listed as 10.
Column D: yes = Positive as Ah receptor antagonist (<250 $\mu$g/mL).
Column E: yes = positive as syncitia formation antagonist (5 < $\mu$g/mL).

TABLE 10

Those compounds showing high Ah-receptor Inhibition and/or high inhibition of HIV cytopathicity.
Cross Products Ratio

|  | Count |
|---|---|
| PP | 7 |
| NN | 6 |
| PN | 1 |
| NP | 5 |
| (PP × NN)/(PN × NP) | 8.4 |

PP = Positive as Ah receptor antagonist and Syncitia antagonist.
NN = Negative as Ah receptor antagonist and Syncitia antagonist.
PN = Positive as Ah receptor antagonist and Negative as Syncitia antagonist.
NP = Negative as Ah receptor antagonist and Positive as Syncitia antagonist.

EXAMPLE 8

Anti-Cancer Effects of Andrographolide and its Synergistic Use with Ah Receptor Antagonists and/or Agonists The extract of the *Andrographis paniculata* plant has been used successfully for the treatment of several types of afflictions, including tumors. One Chinese study describes the use of *Andrographis paniculata* extract for the treatment of chorioepithelioma and chorioadenoma (Yin, J., and Guo, L. (1993) Contemporary Traditional Chinese Medicine. Xie Yuan. Beijing, incorporated herein by reference). Of the 60 cases treated, 47 of the patients (78%) did not experience a regrowth of the tumor within five years and in the other 13 cases *Andrographis paniculata* was not effective.

The use of *Andrographis paniculata* for the successful treatment of an anal tumor has also been reported. An extract of 100 g of *Andrographis paniculata* was prepared by boiling in 500 mL of water. The anal tumor was treated topically in a sitz bath and a cure was reported.

Several research groups have demonstrated the anti-tumor activity of the diterpene lactones isolated from *Andrographis paniculata*, known as Andrographolide (for more information concerning the uses of Andrographolide by the Applicants please see PCT Application (s/n PCT/US95/15915)) which is herein incorporated by reference, and will be supplied in the IDS. This is the reason that this diterpene compound was tested for its effects in conjunction with the Ah receptor agonists and antagonists herein disclosed. Its potent activity against cytopathic changes is disclosed in the above referenced patent application.

EXAMPLE 9

The Ah receptors Inability to Bind or Interact Directly with Andrographolide

A method to screen Andrographolide and Oleanolic Acid was developed in order to test whether these compounds could bind or interact with the Ah receptor. The process involved selecting a discriminating range to determine Ah receptor activity. The range chosen was between 0.313–10 $\mu$g/mL. Table 10 shows the results for the two compounds tested, both in the presence and absence of 0.5nM TCDD. Overall the indications were that Andrographolide does not interact or inhibit the Ah receptor. Thus, the synergistic effects found in regard to slowing down cytopathological change when given in conjunction with Ah receptor antagonists or agonists do not relate to additional binding of the Ah receptor by Andrographolide. The Andrographolide is, in fact, acting in a separate yet synergistic fashion.

TABLE 11

The ability of Andrographolide and Oleanolic Acid to act as Agonists or Antagonists of the Ah Receptor. Andrographolide and Oleanolic Acid were Tested in AhIA with and without the presence of TCDD.

| Test as Antagonists $\mu$g/mL | Tested in the Presence of 0.5 nM TCDD Oleanolic Acid | Milli O.D at 405 Andrographolide |
|---|---|---|
| 10 | 1143 | 1164 |
| 5 | 1423 | 1421 |
| 2.5 | 1462 | 1416 |
| 1.25 | 1438 | 1437 |
| 0.625 | 1444 | 1402 |
| 0.313 | 1493 | 1457 |

| Test as Agonists $\mu$g/mL | Tested in the Absence of TCDD Oleanolic Acid | Milli O.D at 405 Andrographolide |
|---|---|---|
| 10 | 50 | 47 |
| 5 | 49.5 | 55 |
| 2.5 | 49.5 | 54.5 |
| 1.25 | 49 | 59.5 |
| 0.625 | 19.5 | 43 |
| 0.313 | 48 | 49.5 |

EXAMPLE 10

Quercetin as an Ah Receptor Antagonist

Quercetin is a naturally occurring flavone, often found in plant material that is consumed by animals, including humans, on a daily basis. Quercetin, a common constituent of plants, was identified from a TCM extract that was determined to be a Ah receptor antagonist. The chemical configuration of Quercetin, like flavones generally, is composed of two benzene rings linked through a heterocyclicpyrine ring. Quercetin has been shown to be a genotoxic compound, that may initiate carcinogenic activity in certain tissues if administered at high dosages over a prolonged period. (Dunnick, J. K., and Hailey, J. R. 1992, incorporated herein by reference). Previous research has demonstrated that when in the presence of already transformed cells Quercetin has an anti-proliferative effect on those transformed, cancerous cells. (Scambia et al., 1993, incorporated herein by reference).

For the experiments which provided the data for Table 12 quercetin was dissolved in DMSO to 10 mg/mL and tested as in Example 1, which assayed syncytia formation. The tests for Ah receptor antagonist activity used doses of 20, 10, 5 and 2.5 µg/mL. The results indicated that quercetin had antagonistic activity towards the Ah receptor at all doses tried, see Table 12. The IC50 of this compound was approximated at 3 µg/mL.

TABLE 12

Quercetin Interaction with the Ah Receptor

| µg/mL Quercetin used | Milli O.D. Reading |
|---|---|
| 2.5 | 480 |
| 5 | 320 |
| 10 | 260 |
| 20 | 210 |

.5 nM TCDD: 850 Milli O.D., BG subtracted. Optical density read at 450 nm

EXAMPLE 11

The Use of Quercetin in Conjunction with Other Compounds

The Ah receptor antagonist quercetin (Sigma, St. Louis) was tested in combination with two other naturally occurring non-Ah receptor binding compounds, andrographolide and oleanolic acid. Each individual compound as well as combinations of all three compounds (1:1:1 ratio) were dissolved in DMSO and tested in the HIV-1 synctytia formation assay described in Example 1 above. Determination of chemical synergy was performed using Calcusyn (Biosoft, Cambridge UK).

The combination of the three compounds demonstrated greatly enhanced activity against HIV-1 induced cytopathicity, and was shown through the use of statistical analysis utilizing the Calcusyn software. This demonstration of synergy is significant and offers an added benefit in that the amount of each of the given compounds needed to achieve a given result is lessened, thus reducing possible toxicity and/or side effects, for each of the synergistic compounds. This data is shown in Table 13. Table 12 demonstrates that Quercetin, through O.D. readings made with a spectrometer after exposure to Ah receptor, does present antagonistic activity towards the Ah receptor. This activity made it a compound with significant potential to work by itself or in concert with other compounds, such as Andrographolide to inhibit the intracellular cytopathic changes seen in cells infected with AIDS/HIV and/or transformed or cancerous cells.

TABLE 13

Synergistic Effects of non-Ah Receptor Binding Compounds
Synergy Effects

| Compound(s) Used | IC50 (µg/mL) | Dose Reduction Index |
|---|---|---|
| Quercetin | 0.420 | 10.4 |
| Andrographolide | 0.560 | 12.9 |
| Oleanolic Acid | 1.055 | 24.3 |
| Quercetin + Andrographolide + Oleanolic Acid | 0.044 | — |

The foregoing description has been directed to particular embodiments of the invention in accordance with the requirements of the Patent Statutes for the purposes of illustration and explanation. It will be apparent, however, to those skilled in this art that many modifications and changes will be possible without departure from the scope and spirit of the invention. It is intended that the following claims be interpreted to embrace all such modifications and changes.

Literature Cited and Incorporated by Reference

1. Astroff, B., & Safe, S., 6-*Substituted*-1,3,8-*trichlorodibenzofurans as a 2,3,7,8-Tetrachlorodibenzo-p-dioxin Antagonists in the Rat: Structure Activity Relationships*, Toxicology, 59:285–96 (1989).
2. Astroff, B., et al., 6-*Methyl*-1,3,8-*trichlorodibenzofuran as a 2,3,7,8-Tetrachlorodibenzo-p-dioxin Antagonist: Inhibition of the Induction of Rat Cytochrome P-450 Isozymes and Related Monooxygenase Activities*, Mol. Pharm., 33:231–36 (1988).
3. Astroff, B., & Safe, S., *Comparitive Antiestrogenic Activities of 2,3,7,8-Tetrachlorodibenzo-p-dioxin and 6-Methyl-1,3,8-trichlorodibenzofuran in the Female Rat*, Tox. Appl. Pharm. 95:435–43 (1988).
4. Bannister, R., et al., 6-*Methyl*-1,3,8-*trichlorodibenzofuran as a 2,3,7,8-Tetrachlorodibenzo-p-dioxin Antagonist in C57BL/6 Mice*, Toxicology 54:139–50 (1989).
5. Bartek, J., Z. Staskova, G. Draetta, and J. Lukas, *Molecular pathology of the cell cycle in human cancer cells*, Stem. Cells. (Dayt). 11 Suppl 1: 51–58 (1993).
6. Bartlett, R. and P. Nurse, *Yeast as a model system for understanding the control of DNA replication in Eukaryotes*, Bioessays 12: 457–463 (1990).
7. Bauman, J. W. et al., *Inhibitory Effects of 2,3,7,8-Tetrachlorodibenzo-p-dioxin on Rat Hepatocyte Proliferation Induced by 2/3 Partial Hepatectomy*, Cell Proliferation 28 pp. 437–451 (1995).
8. Bjeldanes, L. F., et al., *Aromatic hydrocarbon responsiveness-receptor agonists generated from indole-3-carbinol in vitro and in vivo: Comparisons with 2,3,7, 8-tetrachlorodibenzo-p-dioxin.* Proc. Natl. Acad. Sci. USA 88:9543–9547 (1991).
9. Choudhury, B. R., S. J. Haque, and M. K. Poddar (1987 *In vivo and in vitro effects of kalmegh (Andrographis paniculata) extract and andrographolide on hepatic microsomal drug metabolizing enzymes,*) Planta Med. 53: 135–140.
10. Cohen, D. I., E. Donoghue, H. Tian, V. Kolesnitchenko, H. C. Lane, and L. Wahl (1993) *A biochemical program implicated in HIV-1 envelope-mediated cell death*, Int. Conf. AIDS 9: 200.
11. Cohen, D. I. et al., Science 256 pp.542–545 (1992). *Participation of Tyrosine Phosphorylation in the Cytopathic Effect of Human Immunodeficiency Virus*-1.
12. Connor, R. I. et al., Journal of Virology 67 pp. 1772–1777 (1993).

13. Corbeil, J. et al., *HIV-Induced Apoptosis Requires the CD4 Receptor Cytoplasmic Tail and Is Accelerated by Interaction of CD4 with p56lck,* Journal of Experimental Medicine 183 pp. 39–48 (1996).
14. Dunnick, J. K., and Hailey, J. R., *Toxicity and Carcinogenicity Studies of Quercetin, a Natural Component of Foods,* Fundamental and Appl. Tox. 19, 423–31 (1992).
15. Draetta, G., H. Piwnica-Worms, D. Morrison, B. Druker, T. Roberts, and Beach D., *Human cdc2 protein kinase is a major cell-cycle regulated tyrosine kinase substrate,* Nature 336: 738–744 (1988).
16. Draetta, G., *Cell cycle control in eukaryotes: molecular mechanisms of cdc2 activation,* Trends. Biochem. Sci. 15: 378–383 (1990).
17. DeVito, M. J. et al., *Dose-Response Relationships in Mice Following Subchronic Exposure to 2,3,7,8-Tetrachlorodibenzo-p-dioxin: CYP1A1, CYP1A2, Estrogen Receptor, and Protein Tyrosine Phosphorylation,* Toxicology and Applied Pharmacology 124 pp. 82–90 (1994).
18. Embretson, J., et al., *Massive covert infection helper T lymphocytes and Macrophages by by HIV during the Incubation Period of AIDS,* Nature 362:359–62 (1993).
19. Fernandez-Salguero, P. et al., *Immune System Impairment and Hepatic Fibrosis in Mice Lacking the Dioxin-Binding Ah Receptor,* Science 268 pp. 722–726 (1995).
20. Furukawa, Y., H. Piwnica-Worms, T. J. Ernst, Y. Kanakura, and J. D. Griffin, *cdc2 gene expression at the G1 to S transition in human T lymphocytes,* Science 250: 805–808 (1990).
21. Gasiewicz, T. A. and G. Rucci., *Alpha-Naphthoflavone acts as an antagonist of 2,3,7,8-tetrachloro-dibenzo-p-dioxin by forming an inactive complex with the Ah receptor.* Molecular Pharmacology 40:607–612 (1991).
22. Handa, S. S. and A. Sharma, *Hepatoprotective activity of andrographolide against galactosamine & paracetamol intoxication in rats,* Indian J. Med. Res 92: 284–292 (1990a).
23. Harper, M. E. et al., *Detection of lymphocytes expressing human T-lymphotropic virus type III in lymph nodes and peripheral blood from infected individuals by in situ hybridization,* Proc. Natl. Acad. Sci. 83:772 (1986).
24. Heinkelein, M. et al., Journal of Virology 69 pp. 6925–6931, *Contact of Human Immunodeficiency Virus Type 1-Infected and Uninfected CD4+T Lymphocytes is Highly Cytolytic for Both Cells* (1995).
25. Hivroz, C. et al., *Human Immunodeficiency Virus gp120 and Derived Peptides Activate Protein Tyrosine Kinase p56lck in Human CD4 T Lymphocytes,* European Journal of Immunology 23 pp. 600–607 (1993).
26. Jellinck, P. H. et al., *Ah receptor binding properties of indole carbinols and induction of hepatic estradiol hydroxylation.* Biochem. Pharmacol. 45:1129–1136 (1993).
27. Keyomarsi, K. and A. B. Pardee, *Redundant cyclin overexpression and gene amplification in breast cancer cells,* Proc. Natl. Acad. Sci. U.S.A. 90: 1112–1116 (1993).
28. Kleman, M. I. et al., *Regulation of human dioxin receptor function by indolocarbazoles, receptor ligands of dietary origin,* J. Biol. Chem. 269:5137–5144 (1994).
29. Kolesnitchenko, V. et al., *Human Immunodeficiency Virus 1 Envelope initiated G2-Phase Programmed Cell Death,* Proc. Natl. Acad. Sci., 92:11889–11893 (1995).
30. Kowalski, M. et al., *Attenuation of Human Immunodeficiency Virus Type 1 Cytopathic Effect by a Mutation Affecting the Transmembrane Envelope Glycoprotein,* Journal of Virology 65 pp. 281–291 (1991).
31. Landers, J. P. and N. J. Bunce, *The Ah receptor and the mechanism of dioxin toxicity,* Biochem J. 276:273–287 (1991).
32. Leibovitch, S. A., Guillier, M., Lenormand, J. L., and Leibovitch, M. P., *p34cdc2 protein is complexed with the c-mos protein in rat skeletal muscle,* Oncogene. 8, 2361–2369 (1993).
33. Loyer, P., D. Glaise, S. Cariou, G. Baffet, L. Meijer, and C. Guguen-Guillouzo, *Expression and activation of cdks (1 and 2) and cyclins in the cell cycle progression during liver regeneration,* J. Biol. Chem. 269: 2491–2500 (1994).
34. Lu, Y. F. et al., *Identification of 3'-methoxy-4'-nitroflavone as a pure aryl hydrocarbon (Ah) receptor antagonist and evidence for more than one form of the nuclear Ah receptor in MCF-7 human breast cancer cells.* Arch. Biochem Biophys 316:470–477 (1995).
35. Ma, X. et al, *Protein Tyrosine Phosphorylation as an Indicator of 2,3,7,8-Tetrachloro-p-Dioxin Exposure In Vivo and In Vitro,* Biochemical and Biophysical Research Communications 189 (1) pp. 59–65 (1992).
36. Ma, X. and Babish, J. G., *Acute 2,3,7,8-Tetrachlorodibenzo-p-dioxin Exposure Results in Enhanced Tyrosylphosphorylation and Expression of Murine Hepatic Cyclin Dependent Kinases,* Biochemical and Biophysical Research Communications 197 (3) pp. 1070–1077 (1993).
37. Matsuda, T., M. Kuroyanagi, S. Sugiyama, K. Umehara, A. Ueno, and K. Nishi, *Cell differentiation-inducing diterpenes from Andrographis paniculata Nees,* Chem. Pharm. Bull (Tokyo). 42: 1216–1225 (1994).
38. Merchant, M., and S. Safe. *In vitro inhibition of 2,3,7,8-tetrachlorodibenzo-p-dioxin-induced activity by alpha-naphthoflavone and 6-methyl-1,3,8-trichlorodibenzofuran using an aryl hydrocarbon (Ah)-responsive construct.* Biochem. Pharmacol. 50:663–668 (1995).
39. Mesange, F., et al., *Ligands of the Antiestrogen-Binding Site Are Able to Inhibit Virion Production of Human Immunodeficiency Virus 1-Infected Lymphocytes,* Mol. Pharm. 50:75–79 (1996).
40. Norbury, C. and P. Nurse, *Controls of cell proliferation in yeast and animals,* Ciba. Found. Symp. 150: 168–77 (1990).
41. Norbury, C., J. Blow, and P. Nurse, *Regulatory phosphorylation of the p34cdc2 protein kinase in vertebrates,* EMBO J. 10: 3321–3329 (1991).
42. Norbury, C. and P. Nurse. *Animal cell cycles and their control,* Annu. Rev. Biochem 61: 441–470 (1992).
43. Pardee, A. B., *G1 events and regulation of cell proliferation,* Science 246: 603–608 (1989).
44. Pham, C. D., Arlinghaus, R. B., Zhen, C-F, Guan, K-L and Singh, B., *Characterization of MEK1 phosphorylation by the V-Mos protein,* Oncogene 10:1683–1688 (1995).
45. Poland, A. et al. *Stereospecific, high affinity binding of 2,3,7,8-tetrachlorodibenzo-p-dioxin by hepatic cytosol. Evidence that the binding species is receptor for induction of aryl hydrocarbon hydroxylase.* J. Biol Chem. 251:4936–4946 (1976).
46. Pollenz, R. S. et al., A Mol. Pharmacol. 45:428–438, (1994).
47. Scambia et al., *Quercetin Induces Type-II Estrogen-Binding Sites in Estrogen-Receptor-Negative (MDA-MB231) and Estrogen-Receptor-Positive (MCF-7) Human Breast-Cancer Cell Lines,* Int'l J. Cancer 54 462–66 (1993).

48. Schnittman, S. M., et al., *The Resevoir for HIV-1 in Human Peripheral Blood Is a T cell That Maintains Expression of CD4*, Science 245:305–08 (1989).
49. Tani, Y. et al., *Normal T Cell Receptor-Mediated Signaling in T Cell Lines Stably Expressing HIV-1 Envelope Glycoproteins*, Journal of Immunology 151 pp. 7337–7348 (1993).
50. van den Heuvel, S. and E. Harlow, *Distinct roles for cyclin-dependent kinases in cell cycle control*, Science 262: 2050–2054 (1993).
51. Watson, M. H., S. L. Venance, S. C. Pang, and A. S. Mak, *Smooth muscle cell proliferation. Expression and kinase activities of p34cdc2 and mitogen-activated protein kinase homologues*, Circ. Res 73: 109–117 (1993).
52. Wheelock, G. D. et al., *Bioimmunoassay of Aryl Hydrocarbon (Ah) receptor transformation in vitro by 2,3,7,8-tetrachlorodibenzo-p-dioxin (TCDD)*. Toxicol. Methods 6:41–50 (1996).
53. Williams, R. T., D. A. Carbonaro-Hall, and F. L. Hall, *Co-purification of p34cdc2/p58cyclin A proline-directed protein kinase and the retinoblastoma tumor susceptibility gene product: interaction of an oncogenic serine/threonine protein kinase with a tumor-suppressor protein,* Oncogene. 7: 423–432 (1992).
54. Zacharewski, T. et al., *6-Methyl-1,3,8-trichlorodibenzofuran (MCDF) as an Antiestrogen in Human and Rodent Cancer Cell Lines: Evidence for the Role of the Ah Receptor,* Tox. Appl. Pharm., 113:311–318 (1992).
55. Zacharewski, T. et al., *Induction of cytochrome P450-dependent monooxygenase activities in rat hepatoma H-4-IIE cells in culture by 2,3,7,8-tetrachlorodibenzo-p-dioxin and related compounds: mechanistic studies using radio labeled congeners,* Arch. Biochem. Biophys. 272:344–355 (1989).
56. Babish and Ma, Use of Andrographolide Compounds To Treat or Prevent Pathogenicity of Disease, s/n PCT/US95/15915.

---

What is claimed is:

1. A method of protecting one or more CD4+T cells from the intracellular cytopathic effects of HIV infection, comprising the step of administering an effective amount of a compound capable of binding and acting as an antagonist of the aryl hydrocarbon receptor such that said compound comes into contact with said cell or group of cells and thereby inhibits any virally induced cytopathic changes in said cells; wherein said compound is selected from the group of compounds consisting of:
    a) polychlorinated dibenzo-p-dioxins;
    b) polyhalogenated dibenzofurans;
    c) polychlorinated biphenyls;
    d) the polyhalogenated dibenzofurans with alkyl group substitutions;
    e) the compound 6-t-butyl, 1,3,8-trichlorodibenzofuran;
    f) the compound 6-nitro, 1,3,8-trichlorodibenzofuran;
    g) the compound 6-ethyl, 1,3,8-trichlorodibenzofuran;
    h) the compound 6-cyclohexyl, 1,3,8-trichlorodibenzofuran;
    i) the compound 6-isopropyl, 1,3,8-trichlorodibenzofuran;
    j) the compound 6-methyl, 1,3,8-trichlorodibenzofuran;
    k) the compound 6-propyl, 1,3,8-trichlorodibenzofuran;
    l) the compound 1-bromo, 6-methyl, 3,8-dichlorodibenzofuran; and
    m) the compound 6-butyl, 1,3,8-trichlorodibenzofuran.

2. The method of claim 1 wherein said compound is administered at a dosage range equivalent to or greater than 4 µmol/Kg to 210 μmol/Kg body weight, one to three times per day.

3. The method of claim 1 wherein the administration of said compounds is accomplished through an oral administration of a pharmaceutical formulation, wherein administration of said compound does not cause the Ah receptor to transform into an active form.

4. A method of treating a viral infection comprising the administering of an effective amount of a compound capable of binding and acting as an antagonist of the aryl hydrocarbon receptor such that said compound comes into contact with a cell or group of cells which have been or will be exposed to a viral pathogen where said compound acts to interfere with viral signal transduction pathways, wherein cytopathic changes in said cells are inhibited; wherein said compound is selected from the group of compounds consisting of:

a) polychlorinated dibenzo-p-dioxins;
b) polyhalogenated dibenzofurans;
c) polychlorinated biphenyls;
d) the polyhalogenated dibenzofurans with alkyl group substitutions;
e) the compound 6-t-butyl 1,3,8-trichlorodibenzofuran;
f) the compound 6-nitro, 1,3,8-trichlorodibenzofuran;
g) the compound 6-ethyl, 1,3,8-trichlorodibenzofuran;
h) the compound 6-cyclohexyl, 1,3,8-trichlorodibenzofuran;
i) the compound 6-isopropyl, 1,3,8-trichlorodibenzofuran;
j) the compound 6-methyl, 1,3,8-trichlorodibenzofuran;
k) the compound 6-propyl, 1,3,8-trichlorodibenzofuran;
l) the compound 1-bromo, 6-methyl, 3,8-dichlorodibenzofuran; and
m) the compound 6-butyl, 1,3,8-trichlorodibenzofuran.

5. The method of claim 4 where said viral pathogen is the Human Immunodeficiency Virus.

6. The method of claim 4 where said viral pathogen is either the Herpes Simplex Virus I, or II.

7. The method of claim 4 wherein said compound is administered at a dosage range equivalent to or greater than 4 μmol/Kg to 210 μmol/Kg of body weight, one to three times per day.

8. The method of claim 4 wherein the administration of said compound is accomplished through an oral administration of a pharmaceutical formulation, wherein administration of said compound does not cause the Ah receptor to transform into an active form.

9. A method of treating a viral infection comprising the administration of an effective amount of a first compound capable of binding and acting as an antagonist of the aryl hydrocarbon receptor such that said first compound comes into contact with a cell or group of cells which have been or will be exposed to a viral pathogen where said first compound acts to interfere with virally induced cytopathic changes, in conjunction with a second compound, such that said compounds come into contact with said cell or group of cells, thereby inhibiting virally induced cytopathic changes in said cells; wherein said first compound capable of binding and acting as an antagonist of the aryl hydrocarbon receptor is selected from the group of compounds consisting of:

a) polychlorinated dibenzo-p-dioxins;
b) polyhalogenated dibenzofurans;
c) polychlorinated biphenyls;
d) the polyhalogenated dibenzofurans with alkyl group substitutions;
e) the compound 6-t-butyl, 1,3,8-trichlorodibenzofuran;
f) the compound 6-nitro 1,3,8-trichlorodibenzofuran;
g) the compound 6-ethyl, 1,3,8-trichlorodibenzofuran;
h) the compound 6-cyclohexyl, 1,3,8-trichlorodibenzofuran;
i) the compound 6-isopropyl, 1,3,8-trichlorodibenzofuran;

j) the compound 6-methyl, 1,3,8-trichlorodibenzofuran;

k) the compound 6-propyl, 1,3,8-trichlorodibenzofuran;

l) the compound 1-bromo, 6-methyl, 3,8-dichlorodibenzofuran; and m) the compound 6-butyl, 1,3,8-trichlorodibenzofuran.

10. The method of claim 9 wherein the said second compound is the diterpene lactone Andrographolide.

11. The method of claim 9 wherein the said second compound is Oleanolic Acid.

12. The method of claim 9 wherein the said second compound is known to affect the tubulin polymerization and/or the availability of tubulin subunits on a intracellular level.

13. The method of claim 9 wherein said Ah receptor antagonist is administered at a dosage range equivalent to or greater than 4 μmol/Kg to 200 μmol/Kg body weight, wherein the second compound, Andragrapholide, is administered at a dosage range equivalent to or greater than 1 to 15 mg per kilogram of body, one to three times per day.

14. The method of claim 10 wherein Oleanolic Acid is administered in addition to Andrographolide.

15. A method of protecting one or more CD4+T cells from the intracellular cytopathic effects of HIV infection, comprising the step of administering, in vitro, an effective amount of a compound capable of binding and acting as an antagonist of the aryl hydrocarbon receptor such that said compound comes into contact with said cell or group of cells and thereby inhibits any virally induced cytopathic changes in said cells; wherein said compound is selected from the group of compounds consisting of:

a) polychlorinated dibenzo-p-dioxins;

b) polyhalogenated dibenzofurans;

c) polychlorinated biphenyls;

d) the polyhalogenated dibenzofurans with alkyl group substitutions;

e) the compound 6-t-butyl, 1,3,8-trichlorodibenzofuran;

f) the compound 6-nitro, 1,3,8-trichlorodibenzofuran;

g) the compound 6-ethyl, 1,3,8-trichlorodibenzofuran;

h) the compound 6-cyclohexyl, 1,3,8-trichlorodibenzofuran;

i) the compound 6-isopropyl, 1,3,8-trichlorodibenzofuran;

j) the compound 6-methyl, 1,3,8-trichlorodibenzofuran;

k) the compound 6-propyl, 1,3,8-trichlorodibenzofuran;

l) the compound 1-bromo, 6-methyl, 3,8-dichlorodibenzofuran;

m) the compound 6-butyl, 1,3,8-trichlorodibenzofuran; and n) structural analogs thereof which exhibit the particular biological activity of acting as an aryl hydrocarbon ligand or receptor which is characteristic of polyhalogenated dibenzofurans.

16. The method of claim 15 wherein said compound is administered at a dosage range equivalent to or greater than 4 μmol to 210 μmol of said compound, one to three times per day.

17. The method of claim 15 wherein the administration of said compounds is accomplished through an administration of a pharmaceutical formulation, wherein administration of said compound does not cause the Ah receptor to transform into an active form.

18. A method of reducing virally induced cell cytopathicity comprising administering, in vitro, an effective amount of a compound capable of binding and acting as an antagonist of the aryl hydrocarbon receptor such that said compound comes into contact with a cell or group of cells which have been or will be exposed to a viral pathogen where said compound acts to interfere with viral signal transduction pathways, whereby cytopathic changes in said cells are inhibited; wherein said compound is selected from the group of compounds consisting of:

a) polychlorinated dibenzo-p-dioxins;

b) polyhalogenated dibenzofurans;

c) polychlorinated biphenyls;

d) the polyhalogenated dibenzofurans with alkyl group substitutions;

e) the compound 6-t-butyl, 1,3,8-trichlorodibenzofuran;

f) the compound 6-nitro, 1,3,8-trichlorodibenzofuran;

g) the compound 6-ethyl, 1,3,8-trichlorodibenzofuran;

h) the compound 6-cyclohexyl, 1,3,8-trichlorodibenzofuran;

i) the compound 6-isopropyl, 1,3,8-trichlorodibenzofuran;

j) the compound 6-methyl, 1,3,8-trichlorodibenzofuran;

k) the compound 6-propyl, 1,3,8-trichlorodibenzofuran;

l) the compound 1-bromo, 6-methyl, 3,8-dichlorodibenzofuran;

m) the compound 6-butyl, 1,3,8-trichlorodibenzofuran; and n) structural analogs thereof which exhibit the particular biological activity of acting as an aryl hydrocarbon ligand or receptor which is characteristic of polyhalogenated dibenzofurans.

19. The method of claim 18 where said viral pathogen is the Human Immunodeficiency Virus.

20. The method of claim 18 where said viral pathogen is either the Herpes Simplex Virus I, or II.

21. The method of claim 18 wherein said compound is administered at a dosage range equivalent of 4 μmol to 210 μmol of said compound, one to three times per day.

22. The method of claim 18 wherein the administration of said compound is accomplished through an administration of a pharmaceutical formulation, wherein administration of said compound does not cause the Ah receptor to transform into an active form.

23. A method of reducing virally induced cell cytopathicity comprising the in vitro administration of an effective amount of a first compound capable of binding and acting as an antagonist of the aryl hydrocarbon receptor such that said first compound comes into contact with a cell or group of cells which have been or will be exposed to a viral pathogen where said first compound acts to interfere with virally induced cytopathic changes, in conjunction with a second compound, such that said compounds come into contact with said cell or group of cells, thereby inhibiting virally induced cytopathic changes in said cells; wherein said first compound capable of binding and acting as an antagonist of the aryl hydrocarbon receptor is selected from the group of compounds consisting of:

a) polychlorinated dibenzo-p-dioxins;

b) polyhalogenated dibenzofurans;

c) polychlorinated biphenyls;

d) the polyhalogenated dibenzofurans with alkyl group substitutions;

e) the compound 6-t-butyl, 1,3,8-trichlorodibenzofuran;

f) the compound 6-nitro 1,3,8-trichlorodibenzofuran;

g) the compound 6-ethyl, 1,3,8-trichlorodibenzofuran;

h) the compound 6-cyclohexyl, 1,3,8-trichlorodibenzofuran;
i) the compound 6-isopropyl, 1,3,8-trichlorodibenzofuran;
j) the compound 6-methyl, 1,3,8-trichlorodibenzofuran;
k) the compound 6-propyl, 1,3,8-trichlorodibenzofuran;
l) the compound 1-bromo, 6-methyl, 3,8-dichlorodibenzofuran;
m) the compound 6-butyl, 1,3,8-trichlorodibenzofuran; and
n) structural analogs thereof which exhibit the particular biological activity of acting as an aryl hydrocarbon ligand or receptor which is characteristic of polyhalogenated dibenzofurans.

24. The method of claim 23 wherein the said second compound is the diterpene lactone Andrographolide.

25. The method of claim 23 wherein the said second compound is Oleanolic Acid.

26. The method of claim 23 wherein the said second compound is one known to affect the tubulin polymerization and/or the availability of tubulin subunits on a intracellular level.

27. The method of claim 23 wherein said Ah receptor antagonist is administered at a dosage range equivalent to or greater than 4 μmol to 200 μmol of said Ah receptor antagonist, wherein the second compound, Andrographolide, is administered at a dosage range equivalent to or greater than 1 to 15 mg, one to three times per day.

28. The method of claim 27 wherein Oleanolic Acid is administered in addition to Andrographolide.

29. The method of claim 23 wherein said first compound is administered at a dosage range equivalent to or greater than 4 μmol to 200 μmol of said Ah receptor antagonist, and wherein said second compound is Oleanolic Acid, administered at a dosage range equivalent to or greater than 2.5 mg to 80 mg of said Oleanolic Acid, one to three times per day.

30. The method of claim 9 wherein said first compound is administered at a dosage range equivalent to or greater than 4 μmol to 200 μmol of said receptor Antagonist, and wherein said second compound is Oleanolic Acid, administered at a dosage range equivalent to or greater than 2.5 mg to 80 mg of Oleanolic Acid, one to three times per day.

31. A method of protecting one or more CD4+T cells from the intracellular cytopathic effects of HIV infection, comprising the step of administering an effective amount of a compound capable of binding and acting as an antagonist of the aryl hydrocarbon receptor such that said compound comes into contact with said cell or group of cells and thereby inhibits any virally induced cytopathic changes in said cells; wherein said compound is selected from the group of compounds consisting of:

a) polychlorinated dibenzo-p-dioxins;
b) polyhalogenated dibenzofurans;
c) polychlorinated biphenyls;
d) the polyhalogenated dibenzofurans with alkyl group substitutions;
e) the compound 6-t-butyl, 1,3,8-trichlorodibenzofuran;
f) the compound 6-nitro, 1,3,8-trichlorodibenzofuran;
g) the compound 6-ethyl, 1,3,8-trichlorodibenzofuran;
h) the compound 6-cyclohexyl, 1,3,8-trichlorodibenzofuran;
i) the compound 6-isopropyl, 1,3,8-trichlorodibenzofuran;
j) the compound 6-methyl, 1,3,8-trichlorodibenzofuran;
k) the compound 6-propyl, 1,3,8-trichlorodibenzofuran;
l) the compound 1-bromo, 6-methyl, 3,8-dichlorodibenzofuran; and
m) the compound 6-butyl, 1,3,8-trichlorodibenzofuran.

* * * * *

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v ) FRAGMENT TYPE: internal ( v i ) ORIGINAL SOURCE:
        ( A ) ORGANISM: Guinea Pig
        ( B ) STRAIN: Hartley
        ( F ) TISSUE TYPE: Liver ( i x ) FEATURE:
        ( A ) NAME/KEY: misc_binding (probe)
        ( B ) LOCATION: 1..26

( x i ) SEQUENCE DESCRIPTION: SEQ ID NO:1:

GATCCGGAGT TGCGTGAGAA GAGCCA          26

( 2 ) INFORMATION FOR SEQ ID NO:2:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v ) FRAGMENT TYPE: internal ( v i ) ORIGINAL SOURCE:
    ( A ) ORGANISM: Guinea Pig
    ( B ) STRAIN: Hartley
    ( F ) TISSUE TYPE: Liver ( i x ) FEATURE:
    ( A ) NAME/KEY: misc_binding (probe)
    ( B ) LOCATION: 1..26

( x i ) SEQUENCE DESCRIPTION: SEQ ID NO:2:

TGGCTCTTCT CACGCAACTC CGGATC      2 6